United States Patent
Norman et al.

(10) Patent No.: US 12,410,161 B2
(45) Date of Patent: Sep. 9, 2025

(54) TETRAHYDROBENZO-QUINOLINE SULFONAMIDES DERIVATIVE COMPOUNDS

(71) Applicant: UCB Biopharma SRL, Brussels (BE)

(72) Inventors: Timothy John Norman, Slough (GB); Oliver Philps, Abingdon (GB); Gregory William Haslett, Slough (GB); Jag Paul Heer, Slough (GB); Giancarlo Trani, Abingdon (GB)

(73) Assignee: UCB Biopharma SRL, Brussels (BE)

( * ) Notice: Subject to any disclaimer, the term of this patent is extended or adjusted under 35 U.S.C. 154(b) by 702 days.

(21) Appl. No.: 17/786,295

(22) PCT Filed: Dec. 22, 2020

(86) PCT No.: PCT/EP2020/087691
§ 371 (c)(1),
(2) Date: Jun. 16, 2022

(87) PCT Pub. No.: WO2021/130262
PCT Pub. Date: Jul. 1, 2021

(65) Prior Publication Data
US 2023/0051300 A1 Feb. 16, 2023

(30) Foreign Application Priority Data

Dec. 23, 2019 (GB) ..................... 1919216

(51) Int. Cl.
| | | |
|---|---|---|
| *C07D 413/14* | (2006.01) | |
| *C07D 217/02* | (2006.01) | |
| *C07D 273/04* | (2006.01) | |
| *C07D 401/04* | (2006.01) | |
| *C07D 401/12* | (2006.01) | |
| *C07D 401/14* | (2006.01) | |

(52) U.S. Cl.
CPC ......... *C07D 413/14* (2013.01); *C07D 217/02* (2013.01); *C07D 273/04* (2013.01); *C07D 401/04* (2013.01); *C07D 401/12* (2013.01); *C07D 401/14* (2013.01)

(58) Field of Classification Search
CPC .. C07D 413/14; C07D 217/02; C07D 273/04; C07D 401/04; C07D 401/12; C07D 401/14; C07D 211/06; A61P 11/00
See application file for complete search history.

(56) References Cited

U.S. PATENT DOCUMENTS 4,857,301 A * 8/1989 Czarniecki ........... C07D 401/12
546/139
5,340,811 A   8/1994 Kajihara et al.

FOREIGN PATENT DOCUMENTS

| EP | 0 419 676 | 4/1991 |
| GB | 2270689 | 3/1994 |
| JP | 2007 099676 | 4/2007 |
| WO | WO 2004/058709 | 7/2004 |
| WO | WO 2008/129276 | 10/2008 |

OTHER PUBLICATIONS

Search Report under Section 17 for Great Britian Patent Application No. GB1919216.0 dated Jun. 8, 2020, 2 pages.
Kitagaki Shinji et al., "Intermolecular [4+2] Cycloaddition of o-Quinodimethanes Derived from Ene-Bis (sulfinylallenes)", Journal of Organic Chemistry, vol. 71, No. 18, Sep. 1, 2006, pp. 6908-6914.
Michael P Hay et al: "Tricyclic [1,2,4]triazine 1,4-dixides as hypoxia selective cytotoxins", Journal of Medicinal Chemisgtry, American Chemical Society, US, vol. 51, No. 21, Nov. 13, 2008, pp. 6853-6865.
International Search Report dated Mar. 3, 2021 for International Application No. PCT/EP2020/087691, 3 pages.

* cited by examiner

*Primary Examiner* — Joseph K McKane
*Assistant Examiner* — Anna Grace Kuckla
(74) *Attorney, Agent, or Firm* — McDonnell Boehnen Hulbert & Berghoff LLP

(57) ABSTRACT

The present invention relates to tetrahydrobenzo-isoquinoline sulfonamides derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FIERI receptor.

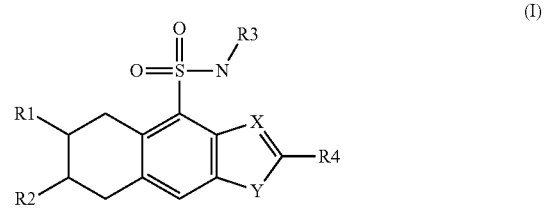

(I)

18 Claims, No Drawings

TETRAHYDROBENZO-QUINOLINE SULFONAMIDES DERIVATIVE COMPOUNDS

CROSS-REFERENCE TO RELATED APPLICATIONS

This application is a U.S. national phase of International Application No. PCT/EP2020/087691, filed Dec. 22, 2020, which claims priority from Great Britain Application No. 1919216.0, filed Dec. 23, 2019, the disclosure of each of which is hereby incorporated by reference in its entirety.

TECHNICAL FIELD

The present invention relates to tetrahydrobenzo-isoquinoline sulfonamides derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

BACKGROUND OF THE INVENTION

IgE (immunoglobulin E) is a member of the immunoglobulin family and mediates allergic responses such as asthma, food allergies, type 1 hypersensitivity and the familiar sinus inflammation.

IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII). Upon exposure of a mammal to an allergen, B-cells are clonally amplified which synthesize IgE that binds the allergen. This IgE in turn is released into the circulation by the B-cells where it is bound by B-cells (through FcεRII) and by mast cells and basophils through the so-called high affinity receptor (FcεRI) found on the surface of the mast cells and basophils. Such mast cells and basophils are thereby sensitized for allergen. The next exposure to the allergen cross-links the FcεRI on these cells and thus activate their release of histamine and other factors which are responsible for clinical hypersensitivity and anaphylaxis.

Currently, allergic diseases, urticaria, and asthma are usually treated with one or more of the following drugs: (1) antihistamines and antileukotrienes which antagonize the inflammatory mediators histamine and leukotrienes, (2) local or systemic (oral or injectable) corticosteroids or immunosuppressants which suppress a broad spectrum of inflammatory mechanisms, (3) short or long-acting bronchodilators which relax smooth muscle of constricted airway in asthma, or (4) mast cell stabilizers which inhibit the degranulation of mast cells that is normally triggered by IgE-binding at FcεRI, (5) biologicals which prevent the binding of IgE at FcεRI. For example, U.S. Pat. No. 4,857,301 describes isoquinoline sulfonamide compounds useful for the treatment of allergy. As another example, U.S. Pat. No. 5,340,811 describes quinolines and isoquinolines that affect the bronchial smooth muscle of a mammal.

However, there is still a need to identify compounds which have therapeutic utility in the treatment or prevention of disorders caused by IgE, particularly disorders caused by the interaction of IgE with the FcεRI receptor.

SUMMARY OF THE INVENTION

It has been found that compounds of formula (I) and their pharmaceutically acceptable salts can be used for this purpose.

DETAILED DESCRIPTION

The present invention provides compounds of formula (I) and pharmaceutically acceptable salts thereof:

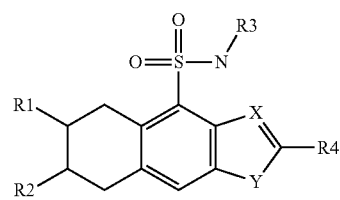

(I)

Wherein
X is C or N;
Y is —(C=N)— or —(N=N)— or O or —(O—NH)—;
R1 represents a group chosen amongst:
Hydrogen; or
Heteroaryl optionally substituted with one or more group chosen amongst amino; C(O)O—C1-6-alkyl; C(O)NH—C1-6-alkyl; NH—C1-6-alkyl; NH—C1-6-alkanediyl-C3-6-cycloalkyl; heteroaryl; NH-heteroaryl optionally substituted with one or more Ra; or
NHC(NCN)NH-Aryl optionally substituted with one or more Ra; or
NH-heteroaryl optionally substituted with one or more groups chosen amongst C1-6-alkyl; heteroaryl optionally substituted with one or more Ra; or
C(O)NH—C1-6-alkyl; or
C(O)NH—C1-6-alkanediyl-aryl optionally substituted with one or more Ra; or
C(O)NH—C1-6-alkanediyl-heteroaryl optionally substituted with one or more Ra; or
NHC(O)heteroaryl optionally substituted with one or more Ra; or
NH—C3-8-cycloalkyl substituted with one or more C1-6-alkylamino; oxo; Ra;
R2 represents a group chosen amongst:
Hydrogen; or C(O)NH—C1-6-alkyl optionally substituted with aryl optionally substituted with one or more Ra; or
Heteroaryl substituted with one or more group chosen amongst heteroaryl optionally substituted with one or more Ra; heteroarylamino optionally substituted with one or more Ra; or
NH-Heteroaryl subtituted with a heteroaryl optionally substituted with one or more Ra; or
R3 represents a group chosen amongst:
C1-6-alkyl optionally substituted with one or more group chosen amongst R3$^a$;
C1-3-alkanediyl-C3-6-cycloalkyl optionally substituted with one or more R3$^a$;
C1-3-alkanediyl-C3-6-heterocycloalkyl optionally substituted with one or more R3$^a$;

C3-6-heterocycloalkyl optionally substituted with one or more R3$^a$;

C3-6-cycloalkyl optionally substituted with one or more R3a;

R3a represents a group chosen amongst hydrogen; halogen; C1-2-alkyl; hydroxy; C1-2-alkoxy R4 represents a group chosen amongst:

C3-6-cycloalkyl optionally substituted with one or more R4$^a$ group; or C1-6-alkanediyl-C3-6-cycloalkyl optionally substituted with one or more R4$^a$ group; or C1-6-alkanediyl-C3-6-heterocycloalkyl optionally substituted with one or more R4$^a$ group;

R4$^a$ represents a group chosen amongst hydroxy; halogen; C1-2-alkyl;

Ra represents a group chosen amongst halogen; nitrile; C1-6-alkyl; C1-6-haloalkyl; C1-6-alkoxy; C1-6-haloalkoxy; C(O)O—C1-6-alkyl; C(O)OH.

According to an embodiment, compounds of the invention are chosen amongst the compounds of formula (I) wherein X is C and Y is —(C═N)—.

According to an embodiment, compounds of the invention are chosen amongst the the compounds of formula (I) wherein wherein X is N and Y is O.

According to an embodiment, compounds of the invention are chosen amongst the the compounds of formula (I) wherein X is N and Y —(O═N)—.

According to an embodiment, compounds of the invention are chosen amongst the the compounds of formula (I) wherein R3 represents C1-6-alkyl optionally substituted with a fluorine atom; other substituents being defined as herein above and below.

According to an embodiment, compounds of the invention are chosen amongst the the compounds of formula (I) wherein R4 represents cyclopropyl; other substituents being defined as herein above and below.

According to an embodiment, compounds of the invention are chosen amongst the the compounds of formula (I) wherein:

when R1 is different than hydrogen, R2 is hydrogen;
when R2 is different than hydrogen, R1 is hydrogen;
other substituents being defined as herein above and below.

The term "pharmaceutically acceptable salt" according to the invention embraces salts of the compounds of formula (I) with a pharmaceutically acceptable acid or base, in particular an acid addition salt. The acid addition salt form of a compound of formula (I) that occurs in its free form as a base can be obtained by treating the free base with an appropriate acid such as an inorganic acid, for example, a hydrohalic acid such as hydrochloric acid or hydrobromic acid, sulfuric acid, nitric acid, phosphoric acid and the like; or an organic acid, such as, for example, acetic acid, trifluoroacetic acid, oxalic acid, hydroxyacetic acid, propanoic acid, lactic acid, pyruvic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and the like.

The invention also relates to all stereoisomeric forms such as enantiomeric and diastereoisomeric forms of the compounds of formula (I) or mixtures thereof (including all possible mixtures of stereoisomers such as racemates). With respect to the present invention reference to a compound or compounds is intended to encompass that compound in each of its possible isomeric forms and mixtures thereof, unless the particular isomeric form is referred to specifically.

Some of the compounds of formula (I) may also exist in tautomeric forms. Such forms although not explicitly indicated in the above formula are intended to be included within the scope of the present invention.

It is to be understood that each individual atom present in formula (I), or in formulae depicted herein, may in fact be present in the form of any of its naturally occurring isotopes, with the most abundant isotope(s) being preferred. Thus, by way of example, each individual hydrogen atom present in formula (I), or in the formulae depicted herein, may be present as a 1H, 2H (deuterium) or 3H (tritium) atom, preferably 1H. Similarly, by way of example, each individual carbon atom present in formula (I), or in the formulae depicted herein, may be present as a 12C, 13C or 14C atom, preferably 12C.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The present invention also includes within its scope prodrug of the compounds of formula (I) above. The term "prodrug" means a compound metabolised in vivo to a compound of the invention or its salt. A prodrug may be identified by administering the prodrug to a mammal, such as rat, mouse, monkey or man, and identifying the compound or its salt, for example in blood or urine.

In the frame of the present invention:

Ct-z represents a carbon chain which may have from t to z carbon atoms, for example a C1-7 carbon chain which may have from 1 to 7 carbon atoms;

Alkyl is a saturated, linear or branched aliphatic group; for example, a C1-6-alkyl group represents a carbon chain of 1 to 6 carbon atoms, linear or branched, for example a methyl, ethyl, propyl, isopropyl, butyl, isobutyl, tertbutyl, pentyl, hexyl. Alkyl encompass deuterated groups, where one or more hydrogen atoms are replaced with deuterium atom $^2$H.

Alkanediyl is a divalent linear or branched saturated hydrocarbon group of general formula $C_nH_{2n}$, such as —CH$_2$—CH$_2$—;

Alkylamino refers to one or more alkyl groups substituted on an amino radical. As examples of alkylamino one can mention methylamino; ethylamino; tertbutylamino; dimethylamino; hydroxy is a —OH group;

hydroxyalkyl is an alkyl group of which one or more hydrogen atom has been substituted with a hydroxy group;

haloalkyl is an alkyl group of which one or more hydrogen atom has been substituted with a halogen atom;

alkoxy, —O-alkyl group;

haloalkoxy is an alkoxy group of which one or more hydrogen atom has been substituted with a halogen atom;

halogen atom, a fluorine, chlorine, bromine or iodine atom;

cycloalkyl refers to a mono or bicyclic aliphatic group that may comprise a double bond without being aromatic and comprising between 3 and 14 atoms, preferably 3 to 9 atoms in the group. As an example of cycloalkyl one can mention cyclopropyl; cyclobutyl; cyclobutenyl; cyclopentyl; cyclohexyl; spiro-undecanyl; spiro-[2.2]pentanyl heterocycloalkyl refers to a mono or bicyclic saturated group comprising between 3 and 14 atoms, preferably 3 to 9 atoms in the group that may comprise a double bond without being aromatic and wherein one or more carbon atom is replaced with an atom chosen amongst nitrogen; oxygen; sulfur. As an example of heterocycloalkyl one can mention aziridinyl; pyrrolidinyl; piperidyl; oxetane; oxaspiro-undecanyl;

hydroxyheterocycloalkyl is an heterocycloalkyl group of which one or more hydrogen atom has been substituted with a hydroxy group;

Heteroaryl refers to a mono- or bicyclic group comprising from 5 to 14 atoms, preferably 5 to 9 atoms wherein at least one ring in the group is aromatic and wherein at least one atom in the group is chosen amongst nitrogen; oxygen; sulfur. As examples of a heteroarylgroup one can mention triazolyl; furanyl; pyrrolyl; chromanyl; isoquinolinyl.

Heteroarylamino refers to an amino group —NH2 substituted with a heteroaryl group. Example of heteroaryl group can be pyridinylamino.

Another embodiment of the present invention concerns a pharmaceutical composition comprising a detectable amount of a compound of formula (I) or a pharmaceutically acceptable salt, solvate or co-crystal thereof in combination with a pharmaceutically acceptable diluent or carrier.

In yet another embodiment, the present invention concerns a compound of formula (I), a pharmaceutically acceptable salt, solvate or co-crystal thereof for use as a medicament, in particular for use in a method for the treatment or prevention of disorders caused by IgE, including allergy, type 1 hypersensitivity, familiar sinus inflammation, urticaria or related conditions, such as airway constriction in asthma, local inflammation in eczema, increased mucus secretion in allergic rhinitis, or increased vascular permeability.

In a further embodiment, the present invention concerns a method for the treatment or prevention of allergy, type 1 hypersensitivity, familiar sinus inflammation, urticaria or related conditions, which comprises the administration of a compound of formula (I) in a therapeutically effective amount.

According to an embodiment, compounds of the invention are chosen amongst the following:
ethyl 5-amino-1-[3-cyclopropyl-5-(2-methylpropylsulfamoyl)-6,7,8,9-tetrahydrobenzo[g]isoquinolin-7-yl]imidazole-4-carboxylate;
3-cyclopropyl-7-[3-[(2,5-dimethylpyrazol-3-yl)amino]-1,2,4-triazol-4-yl]-N-(2-fluoro-2-methylpropyl)-6,7,8,9-tetrahydrobenzo[g]isoquinoline-5-sulfonamide;
2-Cyano-1-[3-cyclopropyl-5-[(2-fluoro-2-methyl-propyl)sulfamoyl]-6,7,8,9-tetrahydrobenzo[g]isoquinolin-7-yl]-3-(p-tolyl)guanidine;
3-cyclopropyl-N-(2-fluoro-2-methylpropyl)-7-[[6-(5-methyl-1,3,4-oxadiazol-2-yl)pyridin-3-yl]amino]-6,7,8,9-tetrahydrobenzo[g]isoquinoline-5-sulfonamide;
3-cyclopropyl-N-(2,2-dimethylpropyl)-5-(2-methylpropylsulfamoyl)-6,7,8,9-tetrahydrobenzo[g]isoquinoline-7-carboxamide;
3-cyclopropyl-N-(2,2-dimethylpropyl)-5-(2-methylpropylsulfamoyl)-6,7,8,9-tetrahydrobenzo[g]isoquinoline-8-carboxamide;
N-benzyl-3-cyclopropyl-5-(2-methylpropylsulfamoyl)-6,7,8,9-tetrahydrobenzo[g]isoquinoline-8-carboxamide;
N-benzyl-3-cyclopropyl-5-(2-methylpropylsulfamoyl)-6,7,8,9-tetrahydrobenzo[g]isoquinoline-7-carboxamide;
2-cyclopropyl-6-[3-[[5-(difluoromethyl)-2-methylpyrazol-3-yl]amino]-1,2,4-triazol-4-yl]-N-(2-methylpropyl)-5,6,7,8-tetrahydrobenzo[f][1,3]benzoxazole-4-sulfonamide;
3-cyclopropyl-N-isobutyl-6,7,8,9-tetrahydro-4H-benzo[g][1,2,4]benzoxadiazine-5-sulfonamide;
N-[3-cyclopropyl-5-(2-methylpropylsulfamoyl)-6,7,8,9-tetrahydrobenzo[g]isoquinolin-7-yl]-6-methyl-1H-indole-3-carboxamide;
3-cyclopropyl-7-[[4-(2,5-dimethylpyrazol-3-yl)-1,2,4-triazol-3-yl]amino]-N-(2-methylpropyl)-6,7,8,9-tetrahydrobenzo[g]isoquinoline-5-sulfonamide;
3-cyclopropyl-7-[3-[(2,5-dimethylpyrazol-3-yl)amino]-1,2,4-triazol-4-yl]-N-(2-methylpropyl)-6,7,8,9-tetrahydrobenzo[g]isoquinoline-5-sulfonamide;
3-cyclopropyl-N-(2-methylpropyl)-7-[3-(pyridin-3-ylamino)-1,2,4-triazol-4-yl]-6,7,8,9-tetrahydrobenzo[g]isoquinoline-5-sulfonamide;
3-cyclopropyl-N-(2-methylpropyl)-7-[(4-pyridin-3-yl-1,2,4-triazol-3-yl)amino]-6,7,8,9-tetrahydrobenzo[g]isoquinoline-5-sulfonamide;
3-cyclopropyl-7-[3-(cyclopropylmethylamino)-1,2,4-triazol-4-yl]-N-(2-methylpropyl)-6,7,8,9-tetrahydrobenzo[g]isoquinoline-5-sulfonamide;
(7R)-3-cyclopropyl-7-[[6-(5-methyl-1,3,4-oxadiazol-2-yl)pyridin-3-yl]amino]-N-(2-methylpropyl)-6,7,8,9-tetrahydrobenzo[g]isoquinoline-5-sulfonamide;
(7S)-3-cyclopropyl-7-[[6-(5-methyl-1,3,4-oxadiazol-2-yl)pyridin-3-yl]amino]-N-(2-methylpropyl)-6,7,8,9-tetrahydrobenzo[g]isoquinoline-5-sulfonamide;
3-cyclopropyl-7-[[2-(ethylamino)-3,4-dioxocyclobuten-1-yl]amino]-N-(2-methylpropyl)-6,7,8,9-tetrahydrobenzo[g]isoquinoline-5-sulfonamide;
3-cyclopropyl-7-[[1-(2,5-dimethylpyrazol-3-yl)imidazo]-2-yl]amino]-N-(2-methylpropyl)-6,7,8,9-tetrahydrobenzo[g]isoquinoline-5-sulfonamide;
3-cyclopropyl-N-(2-methylpropyl)-7-(5-pyridin-3-yl-1H-imidazol-2-yl)-6,7,8,9-tetrahydrobenzo[g]isoquinoline-5-sulfonamide;
3-cyclopropyl-N-(2-methylpropyl)-8-(5-pyridin-3-yl-1H-imidazol-2-yl)-6,7,8,9-tetrahydrobenzo[g]isoquinoline-5-sulfonamide;
3-cyclopropyl-8-[3-[(2,5-dimethylpyrazol-3-yl)amino]-1,2,4-triazol-4-yl]-N-(2-fluoro-2-methylpropyl)-6,7,8,9-tetrahydrobenzo[g]isoquinoline-5-sulfonamide;
3-cyclopropyl-8-[[4-(2,5-dimethylpyrazol-3-yl)-1,2,4-triazol-3-yl]amino]-N-(2-fluoro-2-methyl-propyl)-6,7,8,9-tetrahydrobenzo[g]isoquinoline-5-sulfonamide formic acid.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

The following examples illustrate how the compounds covered by formula I may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Abbreviations

DCM Dichloromethane
THF Tetrahydrofuran
EtOAc Ethyl acetate
MeCN Acetonitrile
MeOH Methanol
br s Broad singlet
hept heptane
M Mass or Molar
Brine Saturated sodium chloride solution
HPLC High performance liquid chromatography
LCMS Liquid Chromatography Mass Spectrometry
DIPEA N,N-di-iso-propylethylamine
RT Retention time
DMF N,N'-dimethylformamide
NaOH Sodium hydroxide
LiOH Lithium hydroxide
TFA Trifluoroacetic acid
DMSO Dimethyl sulfoxide
EtOH Ethanol
sat. saturated
aq. aqueous
tBuXPhos Pd G3 [(2-Di-tert-butylphosphino-2',4',6'-triiso-propyl-1,1'-biphenyl)-2-(2'-amino-1,1' biphenyl)] palladium(II) methanesulfonate
HATU 1-[Bis(dimethylamino)methylene]-1H-1,2,3-triazolo[4,5-b]pyridinium 3-oxid hexafluorophosphate
min minutes
IPA Isopropyl alcohol
SFC Supercritical fluid chromatography
TEA Triethylamine
$Pd_2(dba)_3$ Tris(dibenzylideneacetone)dipalladium(0)
Xantphos 4,5-Bis(diphenylphosphino)-9,9-dimethylxanthene
TBME tert-Butylmethyl ether
KP—NH Biotage® SNAP KP—NH, Flash Chromatography Cartridge Method 1:
X-Bridge C18 Waters 2.1×20 mm, 2.5 µm column
Column Temperature 40° C.
Mobile Phase A: 10 mM Ammonium formate in water+0.1% formic acid
Mobile Phase B: Acetonitrile+5% water+0.1% formic acid

| Gradient program: Flow rate 1 mL/minute | | |
| --- | --- | --- |
| Time | A % | B % |
| 0.00 | 95.00 | 5.00 |
| 1.50 | 5.00 | 95.00 |
| 2.25 | 5.00 | 95.00 |
| 2.50 | 95.00 | 5.00 |

Method 2:
Column Kinetex Core-Shell C18 Part No. 00B-4601-AN 2.1×50 mm, 5 µm
Column Temp 40° C.
Mobile Phase A: Water+0.1% Formic acid
Mobile Phase B: Acetonitrile+0.1% Formic acid
Flow rate 1.2 ml/min
Injection Vol 3 µl
Detection Signal UV 215
PDA Spectrum Range: 210-420 nm step: 1 nm

| Gradient | Time (mins) | % organic |
| --- | --- | --- |
| | 0.00 | 5 |
| | 1.20 | 100 |
| | 1.30 | 100 |
| | 1.31 | 5 |

Method 3:
Mobile Phase A: 0.1% Formic Acid in water
Mobile Phase B: 0.1% Formic Acid in Acetonitrile
Phenomenex, Kinetex-XB C18, 2.1 mm×100 mm, 1.7 µm column
Flow rate: 0.6 mL/min
Column temperature: 40° C.
Injection volume: 1 µL

| Gradient: | Time (minutes): | % A | % B |
| --- | --- | --- | --- |
| | 0.00 | 95 | 5 |
| | 5.30 | 0 | 100 |
| | 5.80 | 0 | 100 |
| | 5.82 | 95 | 5 |
| | 7.00 | 95 | 5 |

UV 215 nM, PDA spectrum 200-400 nm, step: 1 nm
MSD Scan Positive 150-850

Method 4:
X-Bridge C18 Waters 2.1×20 mm, 2.5 µm column
Column Temperature 40° C.
Mobile Phase A: 10 nM Ammonium formate in water+0.1% ammonia solution
Mobile Phase B: Acetonitrile+5% water+0.1% ammonia solution

| Gradient program: Flow rate 1 mL/minute | | |
| --- | --- | --- |
| Time | A % | B % |
| 0.00 | 95.00 | 5.00 |
| 4.00 | 5.00 | 95.00 |
| 5.00 | 5.00 | 95.00 |
| 5.10 | 95.00 | 5.00 |

Method 5:
X-Bridge C18 Waters 2.1×20 mm, 2.5 µM column
Column Temperature 40° C.
Mobile Phase A: 10 mM Ammonium formate in water+0.1% formic acid
Mobile Phase B: Acetonitrile+5% water+0.1% Formic acid

| Gradient program: Flow rate 1 mL/min | | |
| --- | --- | --- |
| Time | A % | B % |
| 0.00 | 95.00 | 5.00 |
| 4.00 | 5.00 | 95.00 |
| 5.00 | 5.00 | 95.00 |
| 5.10 | 95.00 | 5.00 |

Method 6:
Waters UPLC® BEH™ C18, Part No. 186002352, 2.1× 100 mm, 1.7 μm
Column Temperature 40° C.
Mobile Phase A: 2 mM ammonia bicarbonate, buffered to pH 10
Mobile Phase B: Acetonitrile

| Gradient program Flow rate 0.6 mL/Min | | |
|---|---|---|
| Time | A % | B % |
| 0.00 | 95.00 | 5.00 |
| 5.30 | 0 | 100 |
| 5.80 | 0 | 100 |
| 5.82 | 95.00 | 5.00 |
| 7.00 | 95.00 | 5.00 |

Method 7:
Stationary phase: X-Bridge C18 Waters 2.1×20 mm, 2.5 μM column
Mobile Phase A: 10 mM Ammonium formate in water+0.1% Ammonia solution
Mobile Phase B: Acetonitrile+5% water+0.1% Ammonia Solution
Flow rate: 1 mL/min

| Gradient program: | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |

INTERMEDIATES

Intermediate 1

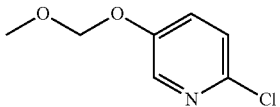

2-chloro-5-(methoxymethoxy)pyridine

A solution of 6-chloropyridin-3-ol (34 g, 262 mmol) and chloromethyl methyl ether (42.3 g, 525 mmol) in DCM (300 mL) was stirred in an ice-bath and N,N diisopropylethylamine (50 mL, 289 mmol) in DCM (50 mL) was added dropwise and stirred for 15 min. The reaction mixture was treated with water, stirred for 10 min, then NaHCO₃ (sat. aq. solution) was added and the mixture stirred for 30 min. The organic layer was separated, and the aqueous layer was extracted with DCM. The combined organic extracts were washed with NaHCO₃ (sat. aq. solution) and dried (MgSO₄). The crude material was purified by column chromatography eluting with a gradient of EtOAc in Hexane to give the title compound (40.5 g, 89% yield) as an oil. $^1$H NMR (400 MHz, Chloroform-d) δ 8.19 (dd, J=3.1, 0.6 Hz, 1H), 7.37 (dd, J=8.7, 3.1 Hz, 1H), 7.31-7.20 (m, 1H), 5.19 (s, 2H), 3.50 (s, 3H).

Intermediate 2

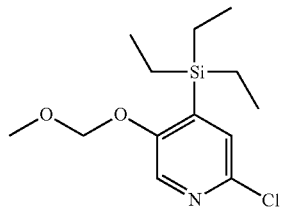 [SMILES: CC[Si](CC)(CC)c1cc(Cl)ncc1OCOC]

[2-chloro-5-(methoxymethoxy)-4-pyridyl]-triethylsilane

A solution of Intermediate 1 (17.2 g, 96.1 mmol) in THF (300 mL) was cooled to −40° C. and treated with a solution of n-butyllithium in hexane (2.5 M, 60 mL, added over 30 mins). After stirring for a further 5 mins, triethylchlorosilane (25 mL, 149 mmol) was added and the reaction mixture was allowed to warm to room temperature. The mixture was quenched by the addition of water (200 mL) and was extracted with EtOAc (2×200 mL). The combined organic extracts were dried over MgSO₄ and concentrated under reduced pressure to give 40 g of the desired product as an impure oil (containing excess silane material.) $^1$H NMR (400 MHz, Chloroform-d) δ 8.15 (s, 1H), 7.21 (d, J=0.5 Hz, 1H), 5.19 (s, 2H), 3.47 (s, 3H), 0.97-0.91 (m, 9H), 0.87-0.79 (m, 6H).

Intermediate 3

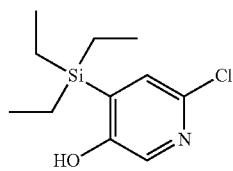

6-chloro-4-triethylsilyl-pyridin-3-ol

To a solution of intermediate 2 (31 g, 97 mmol) in dioxane (100 mL), HCl (4 M in dioxane, 100 mL) was added. The resulting mixture was stirred at room temperature for 16 hours. After this time, a white solid had precipitated. The mixture was diluted with diethyl ether (100 mL) and the resulting solid was removed by filtration (washing with ether) and dried in vacuo to give the title compound as a white solid (13.6 g, 50% yield) which was used in the next step without characterisation.

Intermediate 4

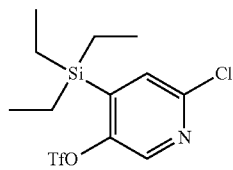 [SMILES: CC[Si](CC)(CC)c1cc(Cl)ncc1OS(=O)(=O)C(F)(F)F]

(6-chloro-4-triethylsilyl-3-pyridyl) trifluoromethanesulfonate

A solution of intermediate 3 (13.6 g, 48.5 mmol) and DIPEA (21 mL, 120.5 mmol) in DCM (250 mL) was cooled to −78° C. and treated with trifluoromethanesulfonic anhydride (1 M in DCM, 100 mL, 100 mmol, added dropwise). After the addition was completed, the mixture was allowed to warm to room temperature, and quenched with NaHCO$_3$ (sat. aq. 100 mL). The layers were separated, and the aqueous phase was extracted with DCM (100 mL). The combined organic extracts were dried over MgSO$_4$, concentrated under reduced pressure and purified by column chromatography eluting with a gradient of EtOAc in Hexane to give the title compound (17.7 g, 97% yield) as a liquid. $^1$H NMR (250 MHz, Chloroform-d) δ 8.37 (s, 1H), 7.39 (s, 1H), 1.03-0.86 (m, 15H).

Intermediate 5

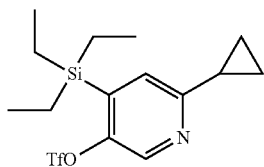 [SMILES: CC[Si](CC)(CC)c1cc(C2CC2)ncc1OS(=O)(=O)C(F)(F)F]

(6-cyclopropyl-4-triethylsilyl-3-pyridyl) trifluoromethanesulfonate

A mixture of intermediate 4 (28.4 g, 75.6 mmol), cyclopropylboronic acid (16 g, 187 mmol), Pd(OAc)$_2$ (850 mg, 3.8 mmol), P(tBu)$_3$.HBF$_4$ (3.3 g, 11.4 mmol) and K$_3$PO$_4$ (40 g, 188.44 mmol) in a biphasic solution of toluene (300 mL) and water (30 mL) was stirred and heated at reflux for 30 minutes. The mixture was cooled to room temperature, the layers were separated and the aqueous was extracted with EtOAc (3×50 mL). The combined organic extracts were dried over MgSO$_4$, filtered through Celite (washing with EtOAc) and concentrated under reduced pressure. Purification by column chromatography eluting with a gradient of EtOAc in Hexane gave the title compound (26.9 g, 93% yield) as an oil. $^1$H NMR (500 MHz, Chloroform-d) δ 8.39 (s, 1H), 7.23 (s, 1H), 2.04 (tt, J=7.8, 5.1 Hz, 1H), 1.06-1.01 (m, 4H), 1.00-0.88 (m, 15H). LCMS [M+H]$^+$ 383, RT 2.43 min (Method 1).

Intermediates 6 & 7

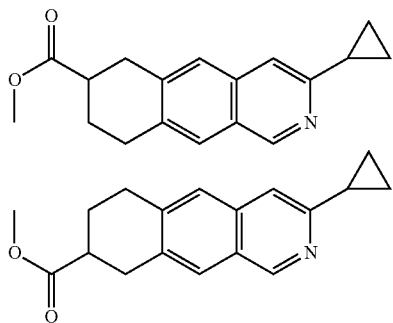

methyl 3-cyclopropyl-6,7,8,9-tetrahydrobenzo[g]isoquinoline-7-carboxylate (6)

methyl 3-cyclopropyl-6,7,8,9-tetrahydrobenzo[g]isoquinoline-8-carboxylate (7)

Caesium fluoride (14.0 g, 94.4 mmol), Ni(cod)$_2$ (0.81 g, 2.94 mmol) and PPh$_3$ (3.14 g, 12.0 mmol) were added to a N$_2$ flushed round bottom flask equipped with a dropping funnel and acetonitrile (100 mL) was added. The mixture was stirred at room temperature for 5 minutes, turning from a yellow solution to dark orange mixture. A solution of Intermediate 5 (12.0 g, 31.5 mmol) and methyl 2-prop-2-ynylhex-5-ynoate (7.75 g, 47.2 mmol) in acetonitrile (100 mL) was added (first 10 mL immediately then the rest dropwise over 10 minutes). The mixture was stirred at room temperature for 3.5 hours after complete substrate addition. The reaction mixture was filtered through Celite and washed through with ethyl acetate. Concentrated under reduced pressure and purified by column chromatography with a gradient of ethyl acetate in heptane to give the title compounds (2.53 g, 29% yield) as a 1:1 mixture of regioisomers. LCMS [M+H]$^+$ 282.2, RT 1.61 min (Method 1).

Intermediates 8 & 9

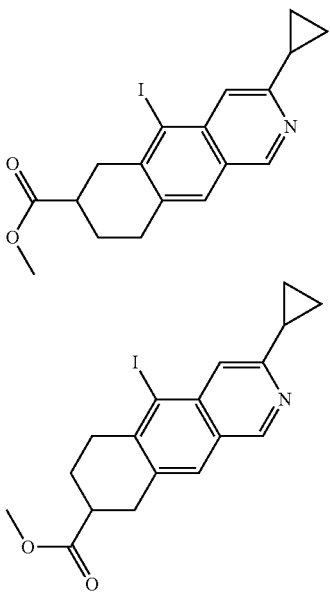

methyl 3-cyclopropyl-5-iodo-6,7,8,9-tetrahydrobenzo[g]isoquinoline-7-carboxylate (8)

methyl 3-cyclopropyl-5-iodo-6,7,8,9-tetrahydrobenzo[g]isoquinoline-8-carboxylate (9)

A mixture of Intermediates 6 & 7 (1:1, 2.53 g, 8.99 mmol) was suspended in acetonitrile (100 mL) and cooled to 0° C. with stirring before adding trifluoromethanesulfonic acid (2.26 mL, 25.6 mmol). The solution was allowed to warm to room temperature before N-iodosuccinimide (3.03 g, 13.5 mmol) was added. The reaction mixture was stirred at room temperature for 18 hours and then quenched with sodium carbonate (2.86 g, 27.0 mmol). The mixture was then filtered through Celite, washed through with acetonitrile and concentrated under reduced pressure. Dichloromethane (100 mL) was added and the solution washed with 10% aqueous sodium thiosulfate (2×50 mL), dried over magnesium sulfate, filtered and concentrated under reduced pressure. Purification by column chromatography with a gradient of ethyl acetate in heptane gave the title compounds (1.98 g, 45% yield) as a 1:1 mixture of regioisomers. LCMS [M+H]$^+$ 408.0, RT 2.08 & 2.12 mins (Method 1).

Intermediates 10 & 11

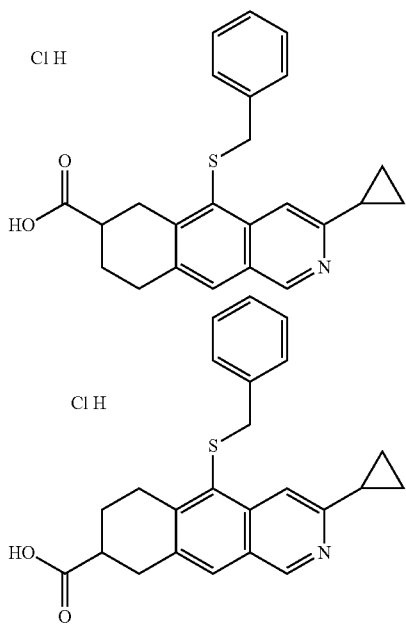

5-benzylsulfanyl-3-cyclopropyl-6,7,8,9-tetrahydrobenzo[g]isoquinoline-7-carboxylic acid hydrochloride (10)

5-benzylsulfanyl-3-cyclopropyl-6,7,8,9-tetrahydrobenzo[g]isoquinoline-8-carboxylic acid hydrochloride (11)

Benzyl mercaptan (0.71 mL, 6.05 mmol) was added to a mixture of Intermediates 8 & 9 (1:1, 83% pure, 1.98 g, 4.04 mmol), DIPEA (2.1 mL, 12.1 mmol), Pd$_2$(dba)$_3$ (111 mg, 0.12 mmol) and Xantphos (140 mg, 0.24 mmol) in dioxane (20 mL). The reaction was then stirred at 100° C. for 2 hours, once at room temperature the mixture was diluted with dichloromethane (20 mL), filtered through Celite, (washing through with dichloromethane) and concentrated under reduced pressure. Purification by column chromatography with a gradient of ethyl acetate in heptane gave a 1:1 mixture of methyl 5-benzylsulfanyl-3-cyclopropyl-6,7,8,9-tetrahydrobenzo[g]isoquinoline-7-carboxylate and methyl 5-benzylsulfanyl-3-cyclopropyl-6,7,8,9-tetrahydrobenzo[g]isoquinoline-8-carboxylate.

The mixture (2.1 g, 4.53 mmol, 87% pure) was then dissolved in THF (25 mL) and 2 M aqueous LiOH (7.0 mL) was added and the solution stirred at room temperature for 16 hours. The mixture was diluted with water (25 mL) and the THF removed under reduced pressure. The residual solution was acidified with 3 M aqueous HCl, resulting in a precipitate which was collected by vacuum filtration and washed with 1 M aqueous HCl. The solids was dissolved in acetonitrile and concentrated under reduced pressure (×2) to give the title compounds (1.94 g, quantitative) as a 1:1 mixture of HCl salt regioisomers. LCMS [M+H]$^+$ 390.2, RT 1.86 & 1.91 mins (Method 1).

Intermediates 12 & 13

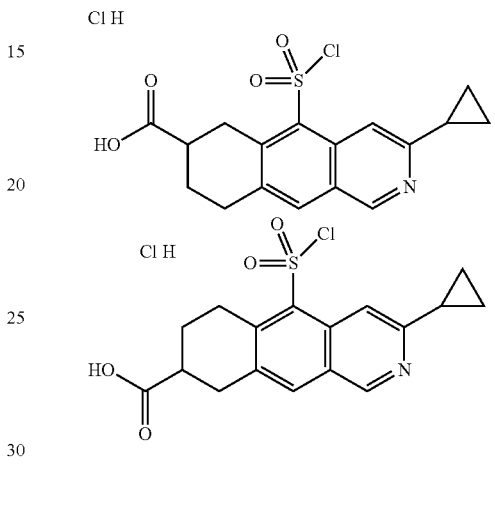

5-chlorosulfonyl-3-cyclopropyl-6,7,8,9-tetrahydrobenzo[g]isoquinoline-7-carboxylic acid hydrochloride (12)

5-chlorosulfonyl-3-cyclopropyl-6,7,8,9-tetrahydrobenzo[g]isoquinoline-8-carboxylic acid hydrochloride (13)

A mixture of intermediates 10 & 11 (1:1, 1.94 g, 4.98 mmol) was suspended in acetonitrile (25 mL) and stirred while cooling in an ice-water bath. Acetic acid (1.63 mL, 28.5 mmol), water (513 µL, 28.5 mmol) and then 1,3-dichloro-5,5-dimethylimidazolidine-2,4-dione (1.96 g, 9.96 mmol) were added and the reaction mixture was stirred at room temperature for 1 hour. The precipitate was collected by vacuum filtration and washed with acetonitrile to give the title compounds (1.43 g, 79% yield) as a 1:1 mixture of HCl salt regioisomers. LCMS [m+H]$^+$366/368, RT 1.90 & 1.93 mins (Method 1).

Intermediates 14 & 15

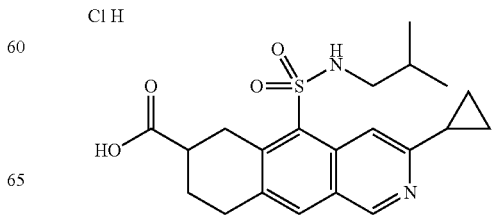

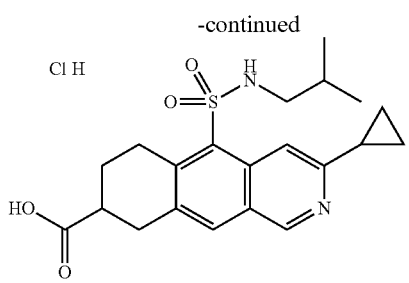

3-cyclopropyl-5-(isobutylsulfamoyl)-6,7,8,9-tetrahydrobenzo[g]isoquinoline-7-carboxylic acid hydrochloride (14)

3-cyclopropyl-5-(isobutylsulfamoyl)-6,7,8,9-tetrahydrobenzo[g]isoquinoline-8-carboxylic acid hydrochloride (15)

2-Methylpropan-1-amine (3.19 mL, 32.1 mmol) was dissolved in dichloromethane (50 mL) and cooled in an ice-water bath with stirring before adding a mixture of intermediates 12 & 13 (1:1, 2.35 g, 6.42 mmol). The mixture was allowed to warm to room temperature and stirred for 10 minutes. The solution was concentrated under reduced pressure and saturated aqueous ammonium chloride (20 mL) was added. The pH was adjusted to pH 4 with 1 M aqueous HCl to give a cloudy mixture and the product was extracted with ethyl acetate (2×100 mL). The combined organic extracts were dried over magnesium sulfate, filtered and concentrated under reduced pressure to give the title compounds (2.65 g, 92% yield, 90% purity) as a 1:1 mixture of HCl salt regioisomers. LCMS [m+H]⁺403.0, RT 1.05 min (Method 2).

Intermediates 16 & 17

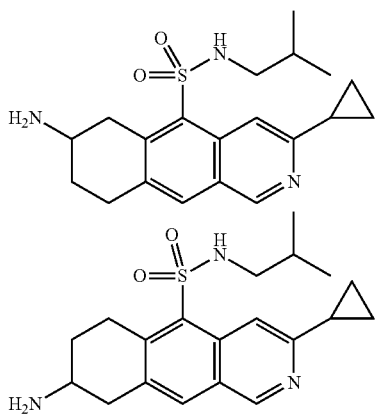

7-amino-3-cyclopropyl-N-isobutyl-6,7,8,9-tetrahydrobenzo[g]isoquinoline-5-sulfonamide (16)

8-amino-3-cyclopropyl-N-isobutyl-6,7,8,9-tetrahydrobenzo[g]isoquinoline-5-sulfonamide (17)

A mixture of intermediates 14 & 15 (1:1, 1.5 g, 3.73 mmol) was dissolved in dry THF (20 mL) before adding DIPEA (1.95 mL, 11.18 mmol) and diphenylphosphoryl azide (0.88 mL, 4.1 mmol). The reaction mixture was heated to reflux with stirring for 3 hours. Once at room temperature the reaction mixture was added to cold 2 M aqueous NaOH (20 mL) and stirred at room temperature for 10 minutes. The pH was adjusted to pH 9-10 and the product was extracted with dichloromethane (2×30 mL). The combined organic extracts were dried over magnesium sulfate, filtered and concentrated under reduced pressure. Purification by column chromatography with a gradient of methanol in dichloromethane gave the title compounds:

Intermediate 16 (465 mg, 32% yield): $\delta_H$ (500 MHz, d$_6$-DMSO) 9.12 (s, 1H), 8.52 (s, 1H), 8.05 (s, 1H), 3.99 (dd, J=17.6, 4.6 Hz, 1H), 3.40-3.33 (m, 1H), 3.21-3.10 (m, 2H), 3.08-2.99 (m, 1H), 2.59 (d, J=6.6 Hz, 2H), 2.29-2.22 (m, 1H), 2.14-2.07 (m, 1H), 1.76-1.66 (m, 1H), 1.62-1.53 (m, 1H), 1.03-0.98 (m, 4H), 0.74-0.71 (m, 6H). 3×exchangeable protons not observed. LCMS [M+H]⁺ 374.2, RT 1.68 min (Method 3).

Intermediate 17 (505 mg, 35% yield): $\delta_H$ (500 MHz, d$_6$-DMSO) 9.08 (s, 1H), 8.57 (s, 1H), 7.98 (s, 1H), 3.60 (dt, J=18.1, 5.5 Hz, 1H), 3.30-3.22 (m, 1H), 3.17-3.08 (m, 2H), 2.73-2.65 (m, 1H), 2.62-2.54 (m, 2H), 2.26-2.18 (m, 1H), 2.00-1.91 (m, 1H), 1.61-1.50 (m, 1H), 1.50-1.41 (m, 1H), 1.02-0.96 (m, 4H), 0.70 (d, J=6.7 Hz, 6H). 3×exchangeable protons not observed. LCMS [m+H]⁺ 374.2, RT 1.64 min (Method 3).

Intermediates 18 & 19

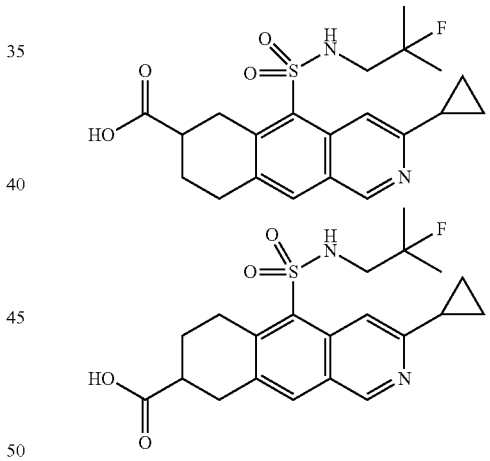

3-cyclopropyl-54(2-fluoro-2-methyl-propyl)sulfamoyl]-6,7,8,9-tetrahydrobenzo[g]isoquinoline-7-carboxylic acid (18)

3-cyclopropyl-54(2-fluoro-2-methyl-propyl)sulfamoyl]-6,7,8,9-tetrahydrobenzo[g]isoquinoline-8-carboxylic acid (19)

2-Fluoro-2-methylpropan-1-amine hydrochloride (0.49 g, 3.85 mmol) was suspended in dichloromethane (40 mL) and DIPEA (1.83 mL, 10.5 mmol) was added. The solution was stirred at room temperature until a clear solution was obtained. A mixture of intermediates 12 & 13 (1:1, 1.28 g, 3.5 mmol) was added portionwise over 5 minutes and the resulting reaction mixture was stirred at room temperature for 15 minutes. The mixture was then concentrated under reduced pressure and 1 M aqueous NaOH (40 mL) was added. The resulting precipitate was removed by vacuum filtration. The filtrate was washed with ethyl acetate (2×50 mL) and then acidified with 3 M aqueous HCl. The solution was extracted with ethyl acetate (3×50 mL) followed by a 1:1 mixture of IPA/chloroform (2×50 mL). The combined organic extracts were dried over magnesium sulfate, filtered and concentrated under reduced pressure. Purification by column chromatography with a gradient of methanol in dichloromethane gave the title compounds (520 mg, 35% yield) as a 1:1 mixture of regioisomers. LCMS [M+H]$^+$ 421.2, RT 1.73 & 1.75 mins (Method 1).

Intermediates 20 & 21

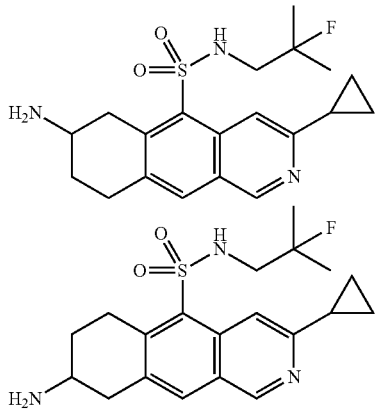

7-amino-3-cyclopropyl-N-(2-fluoro-2-methyl-propyl)-6,7,8,9-tetrahydrobenzo[g]isoquinoline-5-sulfonamide (20)

8-amino-3-cyclopropyl-N-(2-fluoro-2-methyl-propyl)-6,7,8,9-tetrahydrobenzo[g]isoquinoline-5-sulfonamide (21)

A mixture of intermediates 18 & 19 (1:1, 98%, 330 mg, 0.77 mmol) was dissolved in dry THF (15 mL) before adding DIPEA (402 µL, 2.31 mmol) and diphenylphosphoryl azide (182 µl, 0.85 mmol). The reaction mixture was heated to reflux temperature with stirring for 3 hours and then cooled to room temperature. The reaction mixture was added to cold 2 M aqueous NaOH (20 mL) and stirred at room temperature for 10 minutes. The pH was adjusted to pH 9-10 and the product was extracted with dichloromethane (2×30 mL). The combined organic extracts were dried over magnesium sulfate, filtered and concentrated under reduced pressure. Purification by column chromatography with a gradient of methanol in dichloromethane gave the title compounds:

Intermediate 20 (110 mg, 31% yield, 85% purity); $^1$H NMR (500 MHz, d$_6$-DMSO) $\delta_H$ 9.11 (s, 1H), 8.53 (s, 1H), 8.04 (s, 1H), 3.93 (dd, J=17.6, 4.7 Hz, 1H), 3.19-3.09 (m, 3H), 3.06-2.96 (m, 3H), 2.28 (p, J=6.2 Hz, 1H), 2.07 (s, 1H), 1.71-1.61 (m, 1H), 1.16 (d, J=21.4 Hz, 6H), 1.03-0.97 (m, 4H). 3×exchangeable protons not observed. LCMS [M+H]$^+$ 392.2, RT 2.45 min (Method 4).

Intermediate 21 (99 mg, 25% yield, 76% purity); $^1$H NMR (500 MHz, d$_6$-DMSO) $\delta_H$ 9.08 (s, 1H), 8.58 (s, 1H), 7.97 (s, 1H), 3.61 (dt, J=18.1, 5.4 Hz, 1H), 3.28-3.22 (m, 1H), 3.16-3.05 (m, 2H), 3.01-2.94 (m, 2H), 2.71-2.65 (m, 1H), 2.28-2.20 (m, 1H), 1.99-1.91 (m, 1H), 1.50-1.41 (m, 1H), 1.15 (d, J=21.4 Hz, 6H), 1.02-0.97 (m, 4H). 3×exchangeable protons not observed. LCMS [m+H]$^+$ 392.2, RT 2.39 min (Method 4).

Intermediate 22

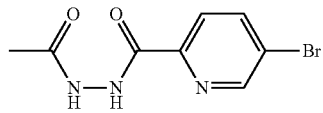

N'-acetyl-5-bromo-pyridine-2-carbohydrazide

Acetohydrazide (0.37 g, 4.99 mmol) was stirred in DCM (10 mL) and DIPEA (0.87 mL, 4.99 mmol). 5-bromopyridine-2-carbonyl chloride (1 g, 4.54 mmol) was added in portions and the reaction was stirred for 15 minutes. The reaction was concentrated under vacuum, then water (10 mL) and DCM (30 mL) were added which resulted in an emulsion, further water and DCM were added resulting in a brown precipitate forming which was collected by vacuum filtration. The filtrate was separated and the DCM layer was concentrated under vacuum to give a brown residue. The aq. layer was added to this residue and sonicated, the resulting brown solid was collected by vacuum filtration and combined with the initial brown solid to afford the title compound (683 mg, 55% yield). $\delta_H$ (250 MHz, d6-DMSO) 10.44 (s, 1H), 9.98 (s, 1H), 8.80 (d, J=1.8 Hz, 1H), 8.28 (dd, J=8.4, 2.3 Hz, 1H), 7.95 (dd, J=8.4, 0.5 Hz, 1H), 1.91 (s, 3H). LCMS [M-acetyl+H]$^+$216.0/218.0, RT 0.67 min (Method 1)

Intermediate 23

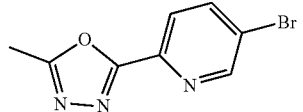

2-(5-bromo-2-pyridyl)-5-methyl-1,3,4-oxadiazole

Intermediate 22 (90%, 856 mg, 2.99 mmol) was stirred in DCM (15 mL), NEt$_3$ (2.8 mL, 20 mmol) was added followed by 4-methylbenzenesulfonyl chloride (700 mg, 3.67 mmol). The reaction was stirred for 3 hours then quenched with saturated aq. NaHCO$_3$ (20 mL) and extracted with DCM (2×20 mL). The organics were dried over sodium sulfate and concentrated under vacuum. Purification by column chromatography using ethyl acetate in heptane afforded the title compound (572 mg, 80% yield). $\delta_H$ (250 MHz, d6-DMSO) 8.91 (dd, J=2.3, 0.7 Hz, 1H), 8.31 (dd, J=8.5, 2.3 Hz, 1H), 8.09 (dd, J=8.5, 0.7 Hz, 1H), 2.61 (s, 3H). LCMS [m+H]$^+$ 240.0/242.0, RT 1.42 min (Method 1)

Intermediate 24

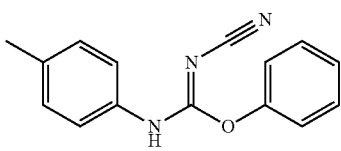 [SMILES: Cc1ccc(N/C(=N/C#N)Oc2ccccc2)cc1]

3-cyano-2-phenyl-1-(p-tolyl)isourea 4-methylaniline (100 mg, 0.93 mmol) was dissolved in dichloromethane (5 mL) and diphenyl cyanocarbonimidate (200 mg, 0.84 mmol) was added. The reaction mixture was stirred at room temperature for 20 hours. The solvent was removed under reduced pressure to give the title compound (300 mg, quantitative, 78% purity). LCMS [m+H]$^+$ 252.0, RT 1.16 min (Method 2).

Intermediate 25

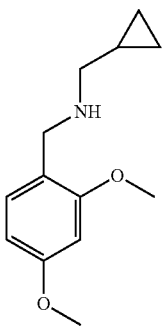 [SMILES: COc1ccc(CNCC2CC2)c(OC)c1]

N-(cyclopropylmethyl)-1-(2,4-dimethoxyphenyl)methanamine 2,4-dimethoxybenzaldehyde (2.0 g, 12.04 mmol), and MgSO$_4$ (400 mg) were added to 1-cyclopropylmethanamine (0.85 g, 12.04 mmol) in ethanol (10 mL). The reaction mixture was stirred at 78° C. for 4 hours. The reaction mixture was cooled to room temperature then sodium borohydride (0.50 g, 13.24 mmol) was added carefully to the reaction mixture. The reaction mixture was stirred overnight at room temperature. The reaction mixture concentrated in vacuo and the residue dissolved in EtOAc (50 mL). The solution was washed with sat. aq. NH$_4$Cl, water and brine (30 mL each) then dried over MgSO$_4$ and concentrate in vacuo. Purification by flash column chromatography eluting with 0% to 20% MeOH in DCM afforded the title compound (2.1 g, 72% yield) as a colourless oil. LCMS [M+H]$^+$ 222, RT 0.83 min (Method 2).

Intermediate 26

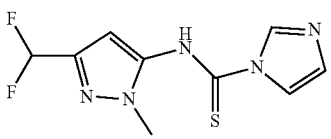 [SMILES: Cn1nc(C(F)F)cc1NC(=S)n1ccnc1]

N-[5-(difluoromethyl)-2-methyl-pyrazol-3-yl]imidazole-1-carbothioamide

A suspension of thiocarbonyl diimidazole (107.3 g, 572 mmol) in DCM (275 mL) was cooled to −10° C. and treated with a solution of 5-(difluoromethyl)-2-methyl-pyrazol-3-amine (42.0 g, 285 mmol) in DCM (210 mL) over 40 min whilst maintaining an internal temperature between −9° C. and −10° C. The resulting mixture was stirred at −10° C. for 18 hours then filtered and the solid washed with DCM (300 mL) to provide the title compound as a pale solid (71.4 g, 49% Yield). LCMS ion observed results from solvolysis by MeOH to give C$_7$H$_9$F$_2$N$_3$OS [M+H]$^+$ 222, RT 0.34 minutes (Method 7).

Intermediate 27

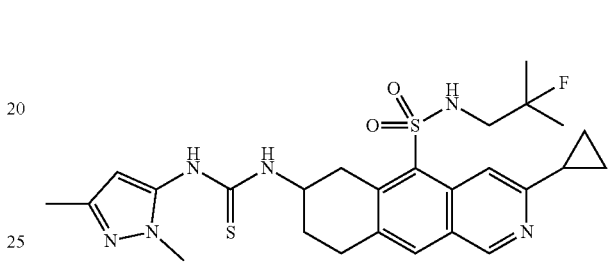

1-[3-cyclopropyl-5-[(2-fluoro-2-methyl-propyl)sulfamoyl]-6,7,8,9-tetrahydrobenzo[g]isoquinolin-7-yl-3-(2,5-dimethylpyrazol-3-yl)thiourea To a suspension of intermediate 20 (49 mg, 0.125 mmol) in anhydrous dichloromethane (3 mL) at room temperature was introduced dry tetrahydrofuran until a homogenous solution was obtained. Diisopropylethylamine (17 mg in 0.5 mL dry dichloromethane, 0.125 mmol) and 5-isothiocyanato-1,3-dimethyl-pyrazole (21 mg in 0.5 mL dry dichloromethane, 0.138 mmol) were then introduced. After 2.5 hours the reaction mixture was treated with a second portion of isothiocyanato-1,3-dimethyl-pyrazole (7 mg in 0.5 mL dry dichloromethane, 0.046 mmol) and the reaction continued for 1.5 hours. The reaction mixture was adsorbed onto silica in-vacuo and the dry-loaded material purified by flash column chromatography using a 50-100% gradient of ethyl acetate in heptane to furnish the title compound (42 mg, 0.068 mmol, 55% yield) as an oil. $^1$H NMR (500 MHz, d-chloroform) δ$_H$ 9.07 (s, 1H), 8.66 (s, 1H), 7.89 (s, 1H), 7.87 (br. s, 1H), 6.60 (s, 1H), 5.94 (s, 1H), 5.78 (s, 1H), 4.68-4.61 (m, 1H), 4.03 (dd, J=17.0, 4.4 Hz, 1H), 3.70 (s, 3H), 3.28 (dd, J=17.0, 9.4 Hz, 1H), 3.16-3.11 (m, 2H), 3.07 (dd, J=19.2, 6.7 Hz, 2H), 2.38-2.31 (m, 1H), 2.30-2.23 (m, 1H), 2.18 (s, 3H), 1.79-1.71 (m, 1H), 1.318 (d, J=21.4 Hz, 3H), 1.312 (d, J=21.4 Hz, 3H), 1.18-1.13 (m, 2H), 1.13-1.09 (m, 2H); LCMS [M+H]$^+$ 545, RT 2.77 min (Method 5).

Intermediate 28

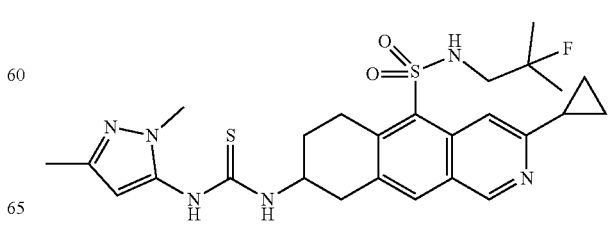

1-[3-cyclopropyl-54(2-fluoro-2-methyl-propyl)sulfa-moyl]-6,7,8,9-tetrahydrobenzo[g]isoquinolin-8-yl]-3-(2,5-dimethylpyrazol-3-yl)thiourea To a stirred solution of intermediate 21 (99 mg, 0.19 mmol, 80% pure) in DCM (4.5 mL) was added DIPEA (33.5 µL, 0.19 mmol), followed by 5-isothiocyanato-1,3-dimethyl-pyrazole (35.3 mg, 0.23 mmol) in DCM (0.5 mL). The reaction mixture was stirred at room temperature for 1 hour, then concentrated under reduced pressure. The residue was purified by column chromatography using a gradient of methanol in TBME to afford the title compound (105 mg, 95% yield) as an off-white powder. $^1$H NMR (500 MHz, CDCl$_3$) $\delta_H$ 9.06-9.01 (m, 1H), 8.50 (s, 1H), 7.82 (s, 1H), 7.38 (s, 1H), 6.19-6.01 (m, 1H), 5.84 (s, 1H), 5.21-5.14 (m, 1H), 4.84-4.74 (m, 1H), 3.87-3.79 (m, 1H), 3.66 (s, 3H), 3.53-3.46 (m, 1H), 3.40-3.31 (m, 1H), 3.14-2.90 (m, 3H), 2.39-2.32 (m, 1H), 2.26-2.20 (m, 1H), 2.15 (s, 3H), 1.77-1.68 (m, 1H), 1.36-1.25 (m, 6H), 1.17-1.12 (m, 2H), 1.09-1.06 (m, 2H). LCMS [m+H]$^+$ 545.1, RT 1.06 min (Method 2).

Intermediate 29

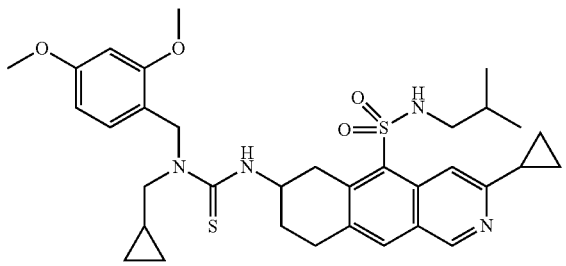 [SMILES: COc1ccc(CN(CC2CC2)C(=S)NC2CCc3cc4cnc(C5CC5)cc4c(S(=O)(=O)NCC(C)C)c3C2)c(OC)c1]

3-[3-cyclopropyl-5-(isobutylsulfamoyl)-6,7,8,9-tetrahydrobenzo[g]isoquinolin-7-yl]-1-(cyclopropylmethyl)-1[(2,4-dimethoxyphenyl)methyl]thiourea To a stirred solution of phenyl chloromethanethioate (0.04 mL, 0.29 mmol) in DCM (5 mL), at 0° C. was added intermediate 16 (100 mg, 0.26 mmol) and triethylamine (0.11 mL, 0.78 mmol) as a solution in DCM (5 mL). The reaction was stirred at 0° C. for 30 minutes, then intermediate 25 (95 mg, 0.24 mmol, 56% purity) was added. The mixture was stirred at 0° C. for 2 hours then warmed to room temperature. A second portion of intermediate 25 (95 mg, 0.24 mmol, 56% purity) was added and the mixture stirred overnight. The solution was then stirred at 40° C. for 36 hours, before a third portion of intermediate 25 (103 mg, 0.26 mmol, 56% purity) was added. The mixture was stirred at 40° C. for a further 2 hours. The mixture was then diluted with water (5 mL) and the aqueous layer extracted with DCM (2×5 mL). The organic fractions were combined, dried over sodium sulphate and purified by column chromatography, using a gradient of TBME in heptanes, to afford the title compound (70 mg, 37% yield, 87% purity) as a white powder. $^1$H NMR (500 MHz, d6-DMSO) $\delta_H$ 9.10 (s, 1H), 8.51 (s, 1H), 8.01 (s, 1H), 7.96-7.90 (m, 1H), 7.22 (d, J=7.6 Hz, 1H), 6.94 (d, J=8.4 Hz, 1H), 6.52 (d, J=2.4 Hz, 1H), 6.45 (dd, J=8.4, 2.4 Hz, 1H), 4.85 (s, 2H), 4.74-4.62 (m, 1H), 3.96 (dd, J=17.6, 4.8 Hz, 1H), 3.77 (s, 3H), 3.72 (s, 3H), 3.19 (dd, J=17.5, 10.1 Hz, 1H), 3.08-3.02 (m, 2H), 2.61 (s, 2H), 2.29-2.20 (m, 1H), 2.07-1.97 (m, 1H), 1.85-1.75 (m, 1H), 1.61-1.53 (m, 1H), 1.07 (s, 1H), 1.01 (d, J=5.3 Hz, 5H), 0.72 (t, J=6.3 Hz, 7H), 0.44-0.38 (m, 2H), 0.25-0.20 (m, 2H). LCMS [M+H]$^+$ 637.3 RT 1.43 min (Method 2).

Intermediate 30

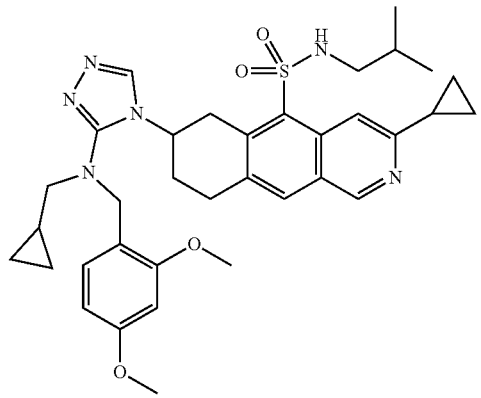 [SMILES: COc1ccc(CN(CC2CC2)c2nncn2C2CCc3cc4cnc(C5CC5)cc4c(S(=O)(=O)NCC(C)C)c3C2)c(OC)c1]

3-cyclopropyl-7-[3-[cyclopropylmethyl-[(2,4-dimethoxyphenyl)methyl]amino]-1,2,4-triazol-4-yl]-N-isobutyl-6,7,8,9-tetrahydrobenzo[g]isoquinoline-5-sulfonamide To a stirred solution of Intermediate 29 (70 mg, 0.1 mmol, 87% purity) in DMF (2 mL) was added formic hydrazide (17.3 mg, 0.29 mmol), followed by mercury dichloride (77.9 mg, 0.29 mmol). The reaction mixture was stirred at room temperature for 5 minutes, then TEA (0.04 mL, 0.29 mmol) was added. The reaction mixture was then stirred at 90° C. for 1 hour, diluted with DCM and Kieselguhr added. The suspension was stirred for 1 minute then filtered. The filtrate was then purified by a KP—NH column, using a gradient of methanol in DCM to afford the title compound (60 mg, 63% yield, 65% purity) as a white powder. LCMS [m+H]$^+$ 645.4, RT 1.23 min (Method 2).

Intermediate 31

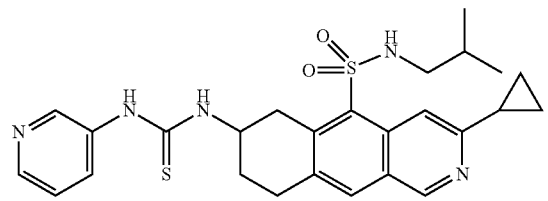 [SMILES: CC(C)CNS(=O)(=O)c1c2c(cc3cnc(C4CC4)cc13)CCC(NC(=S)Nc1cccnc1)C2]

1-[3-cyclopropyl-5-(isobutylsulfamoyl)-6,7,8,9-tetrahydrobenzo[g]isoquinolin-7-yl]-3-(3-pyridyl)thiourea To a solution of intermediate 16 (50 mg, 0.13 mmol) in DCM (3 mL) was added DIPEA (22.6 µL, 0.13 mmol), followed by 3-isothiocyanatopyridine (17.4 µL, 0.16 mmol). The reaction mixture was stirred at room temperature for 1 hour, then purified by column chromatography, using a gradient of methanol in TBME to afford the title compound (37 mg, 55% yield) as a white powder. $\delta_H$ (500 MHz, d6-DMSO) 9.54 (s, 1H), 9.12 (s, 1H), 8.57 (d, J=2.5 Hz, 1H), 8.52 (s, 1H), 8.30-8.26 (m, 1H), 8.15-8.08 (m, 1H), 8.07 (s, 1H), 8.02-7.96 (m, 2H), 7.34 (dd, J=8.2, 4.7 Hz, 1H), 4.58 (s, 1H), 3.95 (dd, J=17.6, 4.6 Hz, 1H), 3.31-3.27 (m, 1H), 3.20-3.06 (m, 2H), 2.65-2.59 (m, 2H), 2.28-2.22 (m, 1H), 2.20-2.13 (m, 1H), 1.87-1.78 (m, 1H), 1.61-1.52 (m, 1H), 1.03-0.99 (m, 4H), 0.71 (d, J=3.2 Hz, 3H), 0.70 (d, J=3.2 Hz, 3H). LCMS [m+H]$^+$ 510.1 RT 1.09 min (Method 2).

Intermediate 32

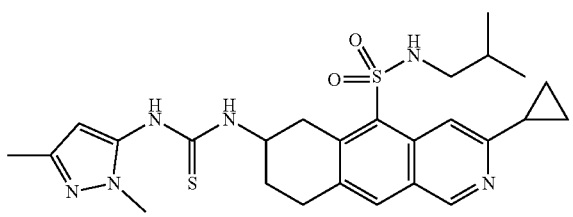 [SMILES: Cc1cc(NC(=S)NC2CCc3cc4cnc(C5CC5)cc4c(S(=O)(=O)NCC(C)C)c3C2)n(C)n1]

1-[3-cyclopropyl-5-(isobutylsulfamoyl)-6,7,8,9-tetrahydrobenzo[g]isoquinolin-7-yl]-3-(2,5-dimethylpyrazol-3-yl)thiourea A solution of intermediate 16 (100 mg, 0.26 mmol) in DCM (4.5 mL) was added DIPEA (45.2 μL, 0.26 mmol), followed by 5-isothiocyanato-1,3-dimethyl-pyrazole (47.7 mg, 0.31 mmol) in DCM (0.5 mL). The reaction mixture was stirred at room temperature for 30 minutes, then purified by column chromatography, using a gradient of methanol in TBME to afford the title compound (120 mg, 75% yield) as a yellow powder. $\delta_H$ (500 MHz, d6-DMSO) 9.16 (s, 1H), 9.11 (s, 1H), 8.52 (s, 1H), 8.05 (s, 1H), 8.03-7.92 (m, 2H), 5.91 (s, 1H), 4.54 (s, 1H), 3.97-3.86 (m, 1H), 3.57-3.51 (m, 3H), 3.26 (dd, J=17.7, 9.6 Hz, 1H), 3.17-3.02 (m, 2H), 2.65-2.57 (m, 2H), 2.28-2.21 (m, 1H), 2.14-2.09 (m, 4H), 2.08 (s, 3H), 1.86-1.76 (m, 1H), 1.57 (hept, J=6.7 Hz, 1H), 1.03-0.98 (m, 4H), 0.74-0.70 (m, 6H). LCMS [M+H]$^+$ 527.1 RT 1.11 min (Method 2).

Intermediate 33

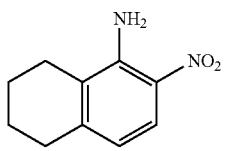 [SMILES: Nc1c([N+](=O)[O-])ccc2c1CCCC2]

6-nitrotetralin-5-amine

A 250 mL three-necked round bottomed flask equipped with a thermometer and a dropping funnel was charged with acetic anhydride (45 mL) and 5,6,7,8-tetrahydronaphthalen-1-amine (6.94 g, 47 mmol) was added dropwise. An orange precipitate soon crashed out and further acetic anhydride (15 mL) was added to aid stirring. The reaction mixture was stirred for 30 minutes. The mixture was then cooled in an ice bath (internal temperature 5° C.) and 90% nitric acid (4.4 mL, 94 mmoL) was added dropwise at such a rate to maintain the internal temperature below 10-12° C. (15 minutes). The reaction mixture was stirred for 15 minutes then it was poured onto ice and allowed to warm to room temperature. The precipitate was filtered under suction and washed with water to afford an orange solid. This was treated with concentrated aq. HCl (100 mL) and refluxed overnight. The mixture was poured onto ice cold water, neutralised with 4 M NaOH and extracted with ethyl acetate (3×150 mL). The combined organic extracts were washed with water (100 mL), brine (80 mL), dried over magnesium sulfate, filtered and concentrated. The crude material was purified by flash chromatography eluting with a gradient of ethyl acetate in heptane to afford the title compound (4.87 g, 54% yield). $\delta_H$ (250 MHz, Chloroform-d) δ 7.93 (d, J=8.9 Hz, 1H), 6.46 (d, J=8.9 Hz, 1H), 6.27 (bs, 2H), 2.74 (t, J=6.1 Hz, 2H), 2.45 (t, J=6.3 Hz, 2H), 1.97-1.84 (m, 2H), 1.83-1.69 (m, 2H). LCMS [M+H]$^+$ 193, RT 1.18 min (Method 2).

Intermediate 34

N-isobutyl-6-nitro-tetralin-5-sulfonamide

To a stirred solution of intermediate 33 (1.50 g, 7.80 mmol) in concentrated aqueous HCl (20 mL) at −5° C. was added a solution of sodium nitrite (590 mg, 8.60 mmol) in water (10 mL) and the resulting mixture was stirred at this temperature for 1 hour, then it was added dropwise to a solution of copper (II) chloride dihydrate (400 mg, 2.34 mmol) and sodium bisulfite (3.30 g, 31.3 mmol) in concentrated aqueous HCl (20 mL) at −5° C. The resulting suspension was allowed to reach room temperature slowly and stirred for 16 hours. The mixture was poured into ice water and extracted with dichloromethane (2×100 mL). The combined organic extracts were dried over magnesium sulfate and concentrated under reduced pressure. The residue was dissolved in dichloromethane (20 mL) and cooled to 0° C. before 2-methylpropan-1-amine (2.00 mL, 20.1 mmol) was added. The solution was warmed to room temperature and washed with 1 M aqueous HCl (50 mL), dried over magnesium sulfate and concentrated under reduced pressure. Purification by column chromatography with a gradient of ethyl acetate in heptane gave the title compound (1.79 g, 73% yield). LCMS [m+H]$^+$ 313.2, RT 1.95 min (Method 1).

Intermediate 35

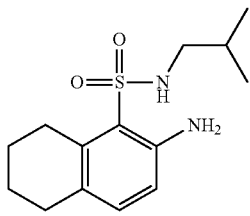 [SMILES: CC(C)CNS(=O)(=O)c1c(N)ccc2c1CCCC2]

6-amino-N-isobutyl-tetralin-5-sulfonamide

To a solution of intermediate 34 (1.79 g, 5.73 mmol) in ethyl acetate (50 mL) was added 10% Pd on charcoal (2 g, 50% wet) and the mixture was stirred under 1 atmosphere of H$_2$ at room temperature for 4 hours. The reaction was flushed with N$_2$ and filtered through a pad of Celite, washed with ethyl acetate and concentrated under reduced pressure to give the title compound (1.7 g, quantitative). LCMS [M+H]$^+$ 283.2, RT 1.93 min (Method 1).

Intermediate 36

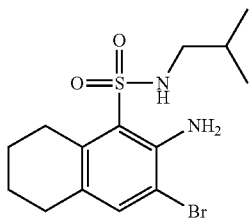 [SMILES: CC(C)CNS(=O)(=O)c1c(N)c(Br)cc2c1CCCC2]

6-amino-7-bromo-N-isobutyl-tetralin-5-sulfonamide

Intermediate 35 (1.53 g, 5.42 mmol) was dissolved in DMF (50 mL) and cooled to 0° C. before N-bromosuccinimide (1.06 g, 5.96 mmol) was added portionwise. The solution was warmed to room temperature and stirred for 30 minutes and then diluted with ethyl acetate (50 mL) and washed with water (50 mL). The aqueous layer was extracted with ethyl acetate (25 mL) and the combined organic extracts were washed with water (50 mL). Dried over magnesium sulfate, filtered and concentrated under reduced pressure. Purification by column chromatography with a gradient of ethyl acetate in heptane gave the title compound (1.40 g, 72% Yield). LCMS [m+H]$^+$ 361/363, RT 2.12 min (Method 1).

Intermediate 37

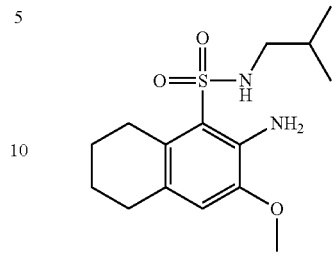

6-amino-N-isobutyl-7-methoxy-tetralin-5-sulfonamide

A mixture of Intermediate 36 (970 mg, 2.68 mmol), iodocopper (51 mg, 0.268 mmol), 1,10-phenanthroline (97 mg, 0.537 mmol) and cesium carbonate (1.75 g, 5.37 mmol) in methanol (5 mL) was heated to 120° C. in a microwave for 8 hours. The reaction was filtered through Celite, washing with methanol and concentrated under reduced pressure before dissolving in dichloromethane (20 mL) and washing with water (20 mL). The solution was passed through a hydrophobic frit and concentrated under reduced pressure. Purification by column chromatography with a gradient of ethyl acetate in heptane gave the title compound (300 mg, 31% Yield). LCMS [m+H]$^+$ 313.0, RT 1.98 min (Method 1).

Intermediate 38

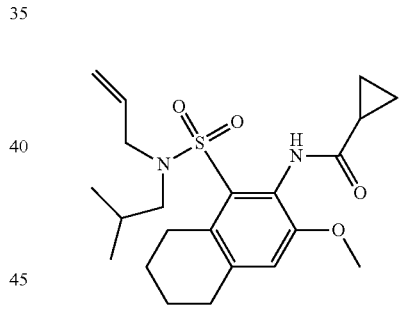

N-[5-[allyl(isobutyl)sulfamoyl]-7-methoxy-tetralin-6-yl]cyclopropanecarboxamide

Intermediate 37 (330 mg, 0.951 mmol) was dissolved in DMF (5 mL) and cesium carbonate (186 mg, 0.570 mmol) followed by 3-bromoprop-1-ene (90 µl, 1.05 mmol) were added. The mixture was stirred at room temperature for 5 hours. Further cesium carbonate (186 mg, 0.570 mmol) was added and stirring continued for 2.5 days at room temperature. The mixture was diluted with ethyl acetate (20 mL) and washed with water (2×20 mL) followed by brine (10 mL). The organic layer was dried over magnesium sulfate, filtered and concentrated under reduced pressure to give an intermediate allyl sulfonamide. This was dissolved in dichloromethane (5 mL) and N-ethyl-N-isopropyl-propan-2-amine (0.25 mL, 1.43 mmol) followed by cyclopropanecarbonyl chloride (104 µL, 1.14 mmol) were added. The solution was stirred for 3 hours at room temperature. Further N-ethyl-N-isopropyl-propan-2-amine (50 µL) and cyclopropanecarbonyl chloride (20 μL) were added and the solution was stirred for 1 hour at room temperature. The solution was purified by column chromatography with a gradient of ethyl acetate in heptane to give the title compound (312 mg, 70% Yield). $\delta_H$ (500 MHz, d-chloroform) 8.35 (s, 1H), 6.86 (s, 1H), 5.68 (ddt, J=16.8, 10.1, 6.6 Hz, 1H), 5.19-5.12 (m, 2H), 3.81 (s, 3H), 3.77 (d, J=6.6 Hz, 2H), 3.07-3.02 (m, 2H), 3.00 (d, J=7.5 Hz, 2H), 2.85-2.78 (m, 2H), 1.87-1.77 (m, 1H), 1.76-1.71 (m, 4H), 1.66-1.56 (m, 1H), 1.04-1.00 (m, 2H), 0.85-0.78 (m, 8H). LCMS [M–H]⁻ 419.0, RT 2.03 min (Method 1).

Intermediate 39

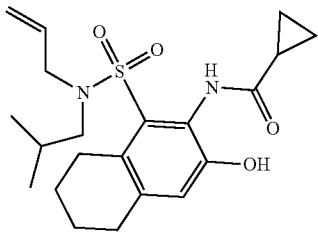

N-[5-[allyl(isobutyl)sulfamoyl]-7-hydroxy-tetralin-6-yl]cyclopropanecarboxamide

Intermediate 38 (312 mg, 0.668 mmol) was dissolved in dichloromethane (15 mL) and a solution of BBr₃ in dichloromethane (1 M, 2.0 mL, 2.00 mmol) added. The reaction mixture was stirred for 0.5 hours and then quenched by addition of water. Dichloromethane (5 mL) was added and the solution passed through a hydrophobic frit. The solvent was concentrated under reduced pressure and the residue purified by column chromatography with a gradient of ethyl acetate in heptane to give the title compound (253 mg, 93% Yield). $\delta_H$ (500 MHz, d-chloroform) 10.45 (s, 1H), 8.64 (s, 1H), 7.02 (s, 1H), 5.67-5.53 (m, 1H), 5.20-5.14 (m, 2H), 3.80 (d, J=6.6 Hz, 2H), 3.04 (t, J=5.9 Hz, 2H), 2.97 (d, J=7.5 Hz, 2H), 2.77 (t, J=6.0 Hz, 2H), 1.85-1.69 (m, 6H), 1.16-1.12 (m, 2H), 0.98-0.94 (m, 2H), 0.78 (d, J=6.6 Hz, 6H). LCMS [M–H]⁻ 405.0, RT 2.01 (Method 1).

Intermediate 40

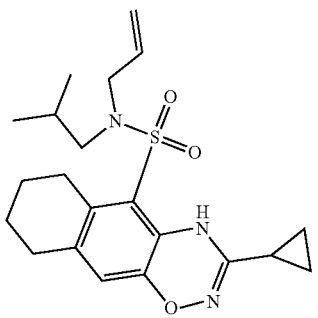

N-allyl-3-cyclopropyl-N-isobutyl-6,7,8,9-tetrahydro-4H-benzo[g][1,2,4]benzoxadiazine-5-sulfonamide Intermediate 39 (233 mg, 0.573 mmol) was dissolved in methanol (3 mL) and potassium tert-butoxide (64 mg, 0.573 mmol) was added. The mixture was allowed to stir for 10 minutes at room temperature before the methanol was removed under reduced pressure. The residue was suspended in 1,4-dioxane (2 mL) and a solution of 2-[(aminooxy)sulfonyl]-1,3,5-trimethylbenzene (222 mg, 1.03 mmol) in 1,4-dioxane (2 mL) added under ice cooling. The ice bath was removed and the solution was allowed to stir for 1 hour. The mixture was concentrated under reduced pressure and the resiude purified by column chromatography with a gradient of dichloromethane in heptane followed by acidic reverse phase column chromatography to give the title compound (50 mg, 22% Yield). $\delta_H$ (500 MHz, d-chloroform) 8.87 (s, 1H), 6.62 (s, 1H), 5.65 (ddt, J=17.0, 10.4, 6.7 Hz, 1H), 5.24-5.16 (m, 2H), 3.80 (d, J=6.7 Hz, 2H), 2.98 (d, J=7.5 Hz, 2H), 2.82 (t, J=5.9 Hz, 2H), 2.64 (t, J=6.0 Hz, 2H), 1.90-1.79 (m, 1H), 1.75-1.65 (m, 4H), 1.54-1.51 (m, 1H), 0.97-0.92 (m, 2H), 0.92-0.86 (m, 2H), 0.83 (d, J=6.7 Hz, 6H). LCMS [m+H]⁺ 404.0, RT 2.22 min (Method 1).

Intermediate 41

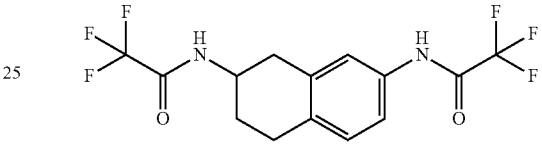

2,2,2-trifluoro-N-[3-[(2,2,2-trifluoroacetyl)amino]tetralin-6-yl]acetamide

To a suspension of 1,2,3,4-tetrahydronaphthalene-2,7-diamine dihydrochloride (CAS 861352-50-3, 15 g, 63.8 mmol) in DCM (150 mL) at 0° C. was added DIPEA (67 mL, 382 mmol). The reaction was stirred for 10 minutes then trifluoroacetic anhydride (19 mL, 134 mmol) was added over 5 minutes. The reaction was stirred at 0° C. for 10 minutes then at room temperature for 2 hours. The reaction was diluted with DCM (150 mL) and washed with 1 N HCl (2×90 mL). At this point a black precipitate crashed out (which was not the desired product). The organic layer was then washed with saturated aqueous NaHCO₃ solution (60 mL) and brine (60 mL). The organic layer was dried (MgSO₄) and the solvent was removed to give a brown gum. Purification by flash column chromatography eluting with 0 to 20% of EtOAc in heptane gradient afforded the title compound as a brown solid (10.5 g, 46% yield). $\delta_H$ (250 MHz, DMSO-d6) 11.15 (s, 1H), 9.50 (d, J=7.9 Hz, 1H), 7.40 (d, J=9.2 Hz, 2H), 7.14 (d, J=8.1 Hz, 1H), 4.17-3.95 (m, 1H), 3.05-2.71 (m, 4H), 1.97 (d, J=11.1 Hz, 2H), 1.82-1.66 (m, 1H). LCMS [M–H]⁻ 353, RT 1.79 minutes (Method 1).

Intermediate 42

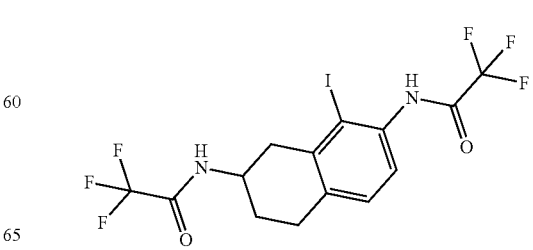

2,2,2-trifluoro-N-[5-iodo-3-[(2,2,2-trifluoroacetyl)amino]tetralin-6-yl]acetamide Intermediate 41 (9.50 g, 26.8 mmol) was dissolved in acetonitrile (200 mL) and N-iodosuccinimide (13.3 g, 59.0 mmol) followed by 4-methylbenzenesulfonic acid monohydrate (5.10 g, 26.8 mmol) were added. The solution was stirred at room temperature for 2.5 days. The solution was then concentrated under reduced pressure and the residue dissolved in ethyl acetate (250 mL). The solution was washed consecutively with saturated aqueous sodium thiosulfate (2×100 mL) and saturated aqueous sodium bicarbonate (100 mL), dried over magnesium sulfate, filtered and concentrated under reduced pressure. Purification by column chromatography with a gradient of ethyl acetate in heptane gave the title compound (1.70 g, 13% Yield). $\delta_H$ (500 MHz, $d_6$-DMSO) 11.21 (s, 1H), 9.59 (d, J=7.4 Hz, 1H), 7.21 (d, J=8.1 Hz, 1H), 7.14 (d, J=8.0 Hz, 1H), 4.15-4.06 (m, 1H), 3.02 (dd, J=17.0, 5.8 Hz, 1H), 2.95-2.83 (m, 2H), 2.65 (dd, J=17.0, 9.6 Hz, 1H), 1.96-1.89 (m, 1H), 1.78-1.67 (m, 1H). LCMS [M−H]⁻ 478.8, RT 2.99 min (Method 1).

Intermediate 43

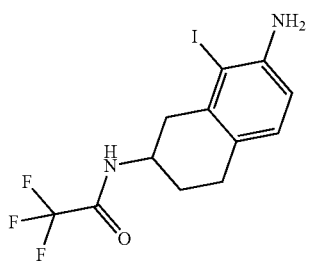 [SMILES: Nc1ccc2c(c1I)CC(NC(=O)C(F)(F)F)CC2]

N-(7-amino-8-iodo-tetralin-2-yl)-2,2,2-trifluoro-acetamide

Intermediate 42 (1.00 g, 2.08 mmol) was dissolved in methanol (10 mL) and 7 M ammonia in methanol (0.89 mL, 6.25 mmol) was added. The solution was heated in a sealed vial at 45° C. for 16 hours then at 55° C. for 2 hours before the solvent was removed under reduced pressure. Purification by column chromatography with a gradient of ethyl acetate in heptane gave the title compound (960 mg, 79% Yield). LCMS [M+H]⁺ 385.0, RT 1.84 min (Method 1).

Intermediate 44

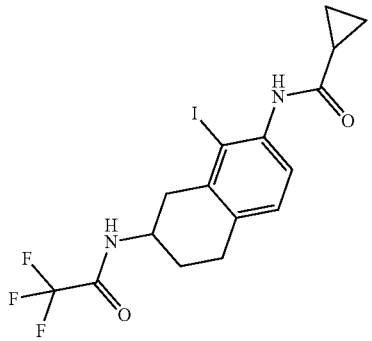

N-[5-iodo-3-[(2,2,2-trifluoroacetyl)amino]tetralin-6-yl]cyclopropanecarboxamide Intermediate 43 (980 mg, 1.68 mmol) was dissolved in dichloromethane (20 mL) and N-ethyl-N-isopropyl-propan-2-amine (382 µL, 2.19 mmol) followed by cyclopropanecarbonyl chloride (168 µL, 1.85 mmol) were added. The solution was stirred at room temperature for 15 minutes before being diluted with dichloromethane (10 mL). Saturated aqueous NaHCO₃ (10 mL) was added and the mixture was passed through a hydrophobic frit and concentrated under reduced pressure. Purification by column chromatography with a gradient of ethyl acetate in heptane gave the title compound (620 mg, 81% Yield). LCMS [M+H]⁺ 453.0, RT 1.84 min (Method 1).

Intermediate 45

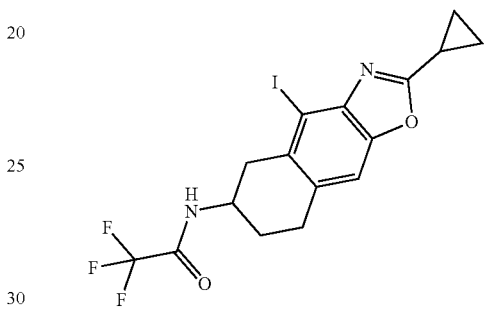

N-(2-cyclopropyl-4-iodo-5,6,7,8-tetrahydrobenzo[f][1,3]benzoxazol-6-yl)-2,2,2-trifluoro-acetamide Intermediate 44 (530 mg, 1.17 mmol) and diacetoxypalladium (27 mg, 0.117 mmol) were added to a solution of dipotassium sulfonatooxy sulfate (475 mg, 1.76 mmol) in a mixture of acetic acid (5.5 mL) and DMF (0.7 mL). The reaction mixture was then treated with trifluoromethanesulfonic acid (104 µL, 1.17 mmol) and heated to 100° C. under air in a sealed tube for 24 hours. Once at room temperature the mixture was filtered through Celite and concentrated under reduced pressure. Purification by column chromatography with a gradient of ethyl acetate in heptane gave the title compound (120 mg, 19% Yield). $\delta_H$ (400 MHz, $d_6$-DMSO) 9.56 (d, J=7.5 Hz, 1H), 7.38 (s, 1H), 4.18-4.04 (m, 1H), 3.07 (dd, J=16.5, 5.9 Hz, 1H), 3.01-2.91 (m, 2H), 2.74-2.64 (m, 1H), 2.31-2.22 (m, 1H), 1.99-1.91 (m, 1H), 1.79-1.65 (m, 1H), 1.21-1.04 (m, 4H). LCMS [M+H]⁺ 451.0, RT 2.00 min (Method 1).

Intermediate 46

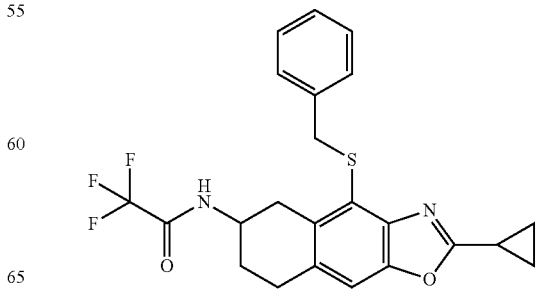

N-(4-benzylsulfanyl-2-cyclopropyl-5,6,7,8-tetrahydrobenzo[f][1,3]benzoxazol-6-yl)-2,2,2-trifluoro-acetamide Benzyl mercaptan (47 µL, 0.400 mmol) and DIPEA (140 µL, 0.800 mmol) were added to a mixture of Intermediate 45 (120 mg, 0.267 mmol), Pd$_2$(dba)$_3$ (15 mg, 16.0 µmol) and Xantphos (19 mg, 32.0 µmol) in 1,4-dioxane (3 mL). The reaction mixture was then heated at 90° C. in a sealed tube for 2 hours with stirring. The mixture was cooled to room temperature and diluted with dichloromethane (10 mL). The solution was filtered through Celite and then concentrated under reduced pressure. Purification by column chromatography with a gradient of ethyl acetate in heptane gave the title compound (110 mg, 92% Yield). δ$_H$ (500 MHz, d$_6$-DMSO) 9.46 (d, J=7.4 Hz, 1H), 7.29 (s, 1H), 7.25-7.13 (m, 5H), 4.47 (s, 2H), 3.98-3.88 (m, 1H), 3.15 (dd, J=16.7, 5.1 Hz, 1H), 2.94-2.89 (m, 2H), 2.57 (dd, J=16.5, 10.3 Hz, 1H), 2.34-2.26 (m, 1H), 1.97-1.88 (m, 1H), 1.72-1.59 (m, 1H), 1.25-1.13 (m, 4H). LCMS [M+H]$^+$ 447.0, RT 2.17 min (Method 1).

Intermediate 47

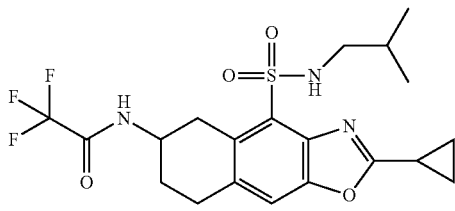

N-[2-cyclopropyl-4-(isobutylsulfamoyl)-5,6,7,8-tetrahydrobenzo[f][1,3]benzoxazol-6-yl]-2,2,2-trifluoro-acetamide Intermediate 46 (100 mg, 0.224 mmol) was dissolved in a mixture of acetonitrile (3 mL) and water (20 µL, 1.12 mmol). Acetic acid (64 µL, 1.12 mmol) was added followed by 1,3-dichloro-5,5-dimethyl-imidazolidine-2,4-dione (88 mg, 0.448 mmol). The reaction mixture was stirred at room temperature for 15 minutes. 2-methylpropan-1-amine (223 µL, 2.24 mmol) was then added and the mixture stirred for 15 minutes at room temperature. The solution was then concentrated under reduced pressure and purified by column chromatography with a gradient of ethyl acetate in heptane to give the title compound (60 mg, 58% Yield). LCMS [M+H]$^+$ 460.0, RT 2.09 min (Method 1).

Intermediate 48

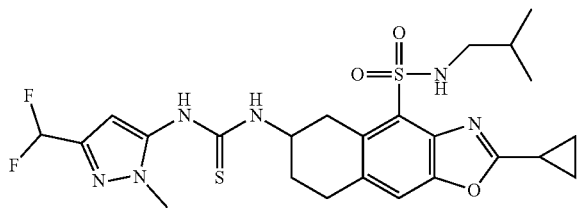

1-[2-cyclopropyl-4-(isobutylsulfamoyl)-5,6,7,8-tetrahydrobenzo[f][1,3]benzoxazol-6-yl]-3-[5-(difluoromethyl)-2-methyl-pyrazol-3-yl]thiourea Intermediate 47 (55 mg, 0.120 mmol) was dissolved in a mixture of methanol (5 mL) and water (0.5 mL). K$_2$CO$_3$ (83 mg, 0.599 mmol) was added and the mixture was stirred in a sealed vial at 60° C. for 3 hours. The solvent was removed under reduced pressure and dichloromethane (10 mL) added. The solution was passed through a hydrophobic frit and the filtrate was treated with intermediate 26 (31 mg, 0.120 mmol) with stirring at room temperature for 5 minutes. The solution was then purified directly by column chromatography with a gradient of ethyl acetate in heptane to give the title compound (45 mg, 65% Yield). LCMS [m+H]$^+$ 553.0, RT 2.08 min (Method 1).

EXAMPLES

Example 1

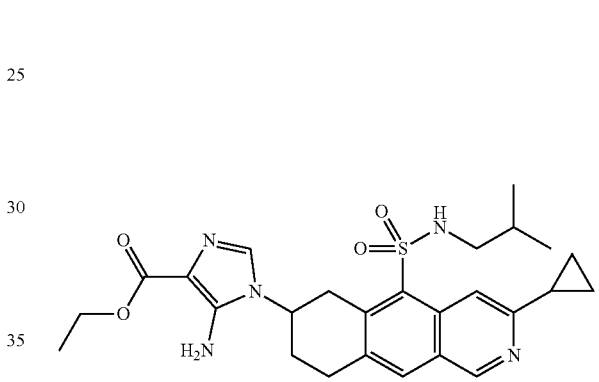

ethyl 5-amino-1-[3-cyclopropyl-5-(2-methylpropylsulfamoyl)-6,7,8,9-tetrahydrobenzo[g]isoquinolin-7-yl]imidazole-4-carboxylate A stock solution of ethyl 2-cyano-2-(dimethoxymethylamino)acetate was prepared: a mixture of Ethyl 2-amino-2-cyano-acetate* (70%, 16.3 mg, 0.09 mmol) and triethylorthoformate (0.01 mL, 0.09 mmol) in CH$_3$CN (1 mL) was heated at 90° C. for 1 hour. The solution was cooled and kept as a stock solution in the fridge (4° C.).

Intermediate 16 (20 mg) was partially dissolved in EtOH (2 mL) and the newly prepared stock solution of ethyl 2-cyano-2-(dimethoxymethylamino)acetate (750 µL) was added. The reaction was stirred for 18 hours. Another portion of the stock solution (250 µL) was added and the reaction was heated at 50° C. for 2 hours. The solvent was removed under vacuum and the residue purified by column chromatography (eluting with 0-100% EtOAc in iso-hexane then 0-10% EtOH in EtOAc) to give the title compound as a white solid (3.3 mg, 10% yield). δ$_H$ (250 MHz, MeOD-d6) 9.07 (s, 1H), 8.64 (s, 1H), 8.08 (s, 1H), 7.21 (s, 1H), 4.62-4.46 (m, 2H), 4.29 (q, J=7.1 Hz, 2H), 4.13 (m, J=17.9, 5.1 Hz, 1H), 3.70 (dd, J=17.5, 9.4 Hz, 1H), 3.26 (d, J=6.9 Hz, 1H), 2.72-2.55 (m, 2H), 2.47-2.19 (m, 3H), 1.60 (dt, J=13.4, 6.7 Hz, 1H), 1.34 (t, J=7.1 Hz, 4H), 1.07 (d, J=6.6 Hz, 4H), 0.76 (dd, J=6.7, 1.5 Hz, 6H). LCMS [m+H]⁺ 512, RT 3.10 minutes (Method 6).

* Prepared according to the procedure in the following patent: WO2008/59368, 2008, A2.

Example 2

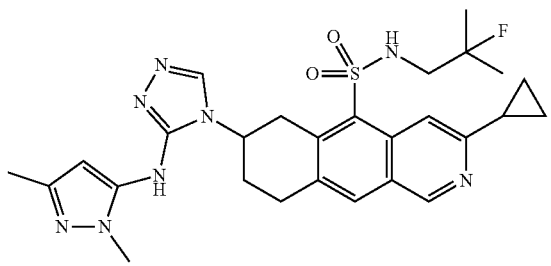 [SMILES: Cc1cc(Nc2nncn2C2CCc3cc4cnc(C5CC5)cc4c(S(=O)(=O)NCC(C)(C)F)c3C2)n(C)n1]

3-cyclopropyl-7-[3-[(2,5-dimethylpyrazol-3-yl)amino]-1,2,4-triazol-4-yl]-N-(2-fluoro-2-methylpropyl)-6,7,8,9-tetrahydrobenzo[g]isoquinoline-5-sulfonamide To a solution of Intermediate 27 (42 mg, 0.068 mmol) in N,N-dimethylformamide (1.5 mL) a solution of formic hydrazide (14 mg, 0.229 mmol) in N,N-dimethylformamide (0.3 mL) followed by mercury(II) chloride (62 mg, 0.229 mmol) were introduced. After 5 minutes stirring at room temperature under an atmosphere of nitrogen, a solution of triethylamine (23 mg, 0.229 mmol) in N,N-dimethylformamide (0.2 mL) was introduced and the reaction warmed to 80° C. for 1.7 hours. After cooling to room temperature, the reaction mixture was diluted with dichloromethane (10 mL), kieselguhr (1.0 g) was introduced, and the suspension stirred for 10 minutes. The suspension was then filtered and the filter-cake washed with dichloromethane (10 mL). Evaporation of the combined filtrates in-vacuo furnished a residue which was purified by low pH preparative liquid chromatography to furnish the title compound (2.3 mg at 88% purity LCMS-UV$_{215}$, 5% yield) as a colourless solid. LCMS [m+H]⁺ 553, RT 2.07 min (Method 3). [Note the title compound was found to be thermally unstable].

Example 3

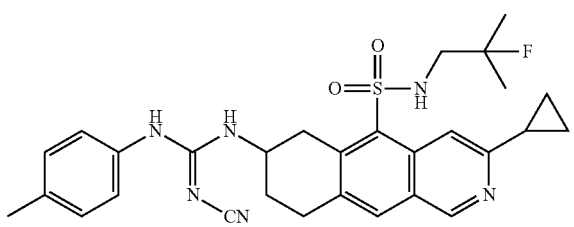 [SMILES: Cc1ccc(N/C(=N/C#N)NC2CCc3cc4cnc(C5CC5)cc4c(S(=O)(=O)NCC(C)(C)F)c3C2)cc1]

2-Cyano-1-[3-cyclopropyl-5-[(2-fluoro-2-methylpropyl)sulfamoyl]-6,7,8,9-tetrahydrobenzo[g]isoquinolin-7-yl]-3-(p-tolyl)guanidine Intermediate 20 was dissolved in IPA (1 mL) in a sealable tube and Intermediate 24 (19.3 mg, 0.08 mmol) was added. The tube was sealed and heated to 100° C. for 2 hours before cooling to room temperature. The mixture was concentrated under reduced pressure and purified by column chromatography with a gradient of ethyl acetate in heptane to give the title compound (10 mg, 23%). δ$_H$ (500 MHz, d$_6$-DMSO) 9.10 (s, 1H), 8.98 (s, 1H), 8.56 (s, 1H), 8.35 (s, 1H), 8.03 (s, 1H), 7.22-7.15 (m, 1H), 7.12 (s, 4H), 4.14-4.03 (m, 1H), 3.92 (dd, J=17.6, 4.7 Hz, 1H), 3.27-3.19 (m, 1H), 3.15-3.02 (m, 2H), 2.99 (d, J=19.8 Hz, 2H), 2.31-2.23 (m, 4H), 2.09-2.01 (m, 1H), 1.86-1.74 (m, 1H), 1.18 (d, J=21.4 Hz, 3H), 1.15 (d, J=21.4 Hz, 3H), 1.05-0.97 (m, 4H). LCMS [M+H]⁺ 549.3, RT 3.27 min (Method 3).

Example 4

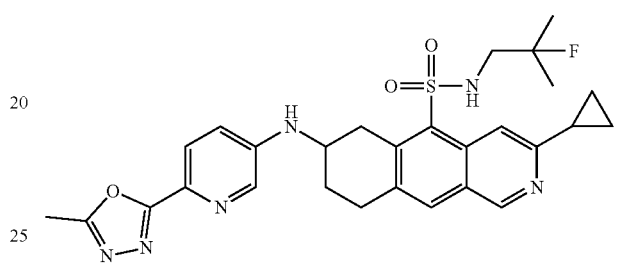

3-cyclopropyl-N-(2-fluoro-2-methylpropyl)-7-[[6-(5-methyl-1,3,4-oxadiazol-2-yl)pyridin-3-yl]amino]-6,7,8,9-tetrahydrobenzo[g]isoquinoline-5-sulfonamide Intermediate 20 (50 mg, 0.13 mmol), Intermediate 23 (43 mg, 0.18 mmol), tBuONa (37 mg, 0.38 mmol) and tBuXPhos Pd G3 (15 mg, 0.02 mmol) were dissolved in a mixture of dioxane (3 mL) and tBuOH (1.5 mL). The reaction mixture was stirred at room temperature for 16 hours. The reaction mixture was then diluted with ethyl acetate and filtered through Celite, washing with ethyl acetate. The solution was concentrated under reduced pressure and the residue purified by column chromatography (eluting with a gradient of ethyl acetate in heptane) followed by reverse phase HPLC (acidic conditions) to give the title compound (5.5 mg, 8% yield). δ$_H$ (500 MHz, d$_6$-DMSO) 9.13 (s, 1H), 8.54 (s, 1H), 8.32 (s, 1H), 8.15 (d, J=2.7 Hz, 1H), 8.08 (s, 1H), 7.84 (d, J=8.7 Hz, 1H), 7.14 (dd, J=8.8, 2.8 Hz, 1H), 6.79 (d, J=7.7 Hz, 1H), 3.96 (dd, J=17.3, 4.6 Hz, 1H), 3.91-3.82 (m, 1H), 3.29-3.24 (m, 1H), 3.20-3.09 (m, 2H), 3.00-2.90 (m, 2H), 2.54 (s, 3H), 2.31-2.23 (m, 1H), 2.22-2.14 (m, 1H), 1.77-1.66 (m, 1H), 1.14 (d, J=21.4 Hz, 3H), 1.11 (d, J=21.4 Hz, 3H), 1.04-0.96 (m, 4H). LCMS [m+H]⁺ 551.4, RT 2.87 min (Method 3).

Examples 5 & 6

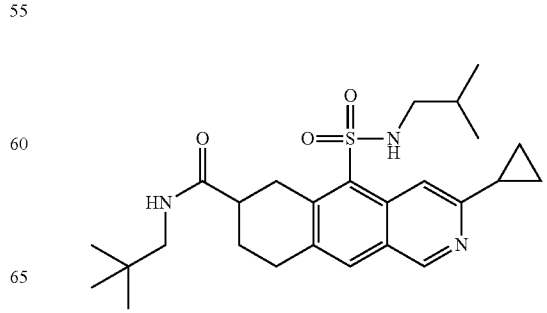

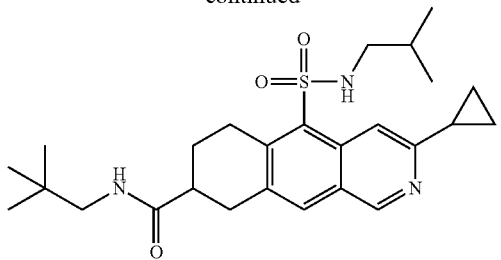
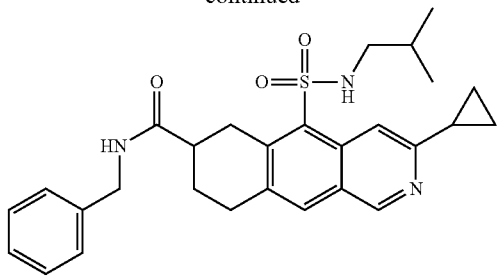

3-cyclopropyl-N-(2,2-dimethylpropyl)-5-(2-methyl-propylsulfamoyl)-6,7,8,9-tetrahydrobenzo[g]isoquinoline-7-carboxamide (5)

3-cyclopropyl-N-(2,2-dimethylpropyl)-5-(2-methyl-propylsulfamoyl)-6,7,8,9-tetrahydrobenzo[g]isoquinoline-8-carboxamide (6)

A solution of intermediates 14 & 15 (100 mg, 0.25 mmol) and DIPEA (87 μL, 0.5 mmol) in dichloromethane (2 mL) was treated with HATU (104 mg, 0.27 mmol) and stirred for 10 minutes at room temperature. 2,2-Dimethylpropan-1-amine (32 μL, 0.27 mmol) was then added and the solution was stirred at room temperature for 1 hour. The solution was washed with saturated aqueous NH₄Cl (2 mL), filtered through a hydrophobic frit and purified by column chromatography (eluting with a gradient of ethyl acetate in heptane) followed by preparative HPLC (acidic conditions) to give the title compounds:

Example 5 (16.7 mg, 14% yield): $\delta_H$ (500 MHz, d₆-DMSO) 9.10 (s, 1H), 8.54 (s, 1H), 8.01 (s, 1H), 7.98 (t, J=5.5 Hz, 1H), 7.85 (t, J=6.2 Hz, 1H), 3.74 (dd, J=17.7, 5.0 Hz, 1H), 3.32-3.26 (m, 1H), 3.09-2.94 (m, 3H), 2.88 (dd, J=13.0, 6.0 Hz, 1H), 2.70-2.54 (m, 3H), 2.29-2.20 (m, 1H), 1.99-1.89 (m, 1H), 1.84-1.74 (m, 1H), 1.63-1.51 (m, 1H), 1.06-0.96 (m, 4H), 0.86 (s, 9H), 0.73 (d, J=6.5 Hz, 3H), 0.72 (d, J=6.4 Hz, 3H). LCMS [M+H]⁺ 472.4, RT 3.58 min (Method 3).

Example 6 (23.6 mg, 20% yield): $\delta_H$ (500 MHz, d₆-DMSO) 9.09 (s, 1H), 8.57 (s, 1H), 8.04 (s, 1H), 7.96 (t, J=5.8 Hz, 1H), 7.84 (t, J=6.2 Hz, 1H), 3.51 (dt, J=17.7, 5.5 Hz, 1H), 3.41-3.37 (m, 1H), 3.07 (d, J=7.8 Hz, 2H), 2.97-2.87 (m, 2H), 2.74-2.65 (m, 1H), 2.61-2.55 (m, 2H), 2.27-2.19 (m, 1H), 2.01-1.92 (m, 1H), 1.84-1.74 (m, 1H), 1.61-1.50 (m, 1H), 1.03-0.97 (m, 4H), 0.85 (s, 9H), 0.70 (d, J=6.7 Hz, 6H). LCMS [M+H]⁺ 472.4, RT 3.42 min (Method 3).

Examples 7 & 8

N-benzyl-3-cyclopropyl-5-(2-methylpropylsulfamoyl)-6,7,8,9-tetrahydrobenzo[g]isoquinoline-8-carboxamide N-benzyl-3-cyclopropyl-5-(2-methylpropylsulfamoyl)-6,7,8,9-tetrahydrobenzo[g]isoquinoline-7-carboxamide A solution of Intermediates 14 & 15 (100 mg, 0.25 mmol) and DIPEA (87 μL, 0.5 mmol) in dichloromethane (2 mL) was treated with HATU (104 mg, 0.27 mmol) and stirred for 10 minutes at room temperature. Benzylamine (30 μL, 0.27 mmol) was then added and the solution was stirred at room temperature for 1 hour. The solution was washed with saturated aqueous NH₄Cl (2 mL), filtered through a hydrophobic frit and purified by column chromatography (eluting with a gradient of ethyl acetate in heptane) followed by prepative HPLC (acidic conditions) to give the title compounds:

Example 7 (26.2 mg, 21% yield): $\delta_H$ (500 MHz, d₆-DMSO) 9.10 (s, 1H), 8.57 (s, 1H), 8.48 (t, J=5.9 Hz, 1H), 8.04 (s, 1H), 7.97 (t, J=5.9 Hz, 1H), 7.35-7.30 (m, 2H), 7.28-7.22 (m, 3H), 4.31 (d, J=5.9 Hz, 2H), 3.53 (dt, J=17.6, 5.5 Hz, 1H), 3.40-3.36 (m, 1H), 3.15-3.06 (m, 2H), 2.73-2.65 (m, 1H), 2.61-2.56 (m, 2H), 2.28-2.18 (m, 1H), 2.04-1.96 (m, 1H), 1.87-1.77 (m, 1H), 1.61-1.50 (m, 1H), 1.03-0.96 (m, 4H), 0.71 (d, J=6.7 Hz, 6H). LCMS [m+H]⁺ 492.3, RT 3.30 min (Method 3).

Example 8 (20.4 mg, 17% yield): $\delta_H$ (500 MHz, d₆-DMSO) 9.10 (s, 1H), 8.54 (s, 1H), 8.48 (t, J=5.9 Hz, 1H), 8.01 (s, 1H), 7.98 (t, J=6.0 Hz, 1H), 7.36-7.29 (m, 2H), 7.29-7.21 (m, 3H), 4.35 (dd, J=15.2, 6.0 Hz, 1H), 4.28 (dd, J=15.2, 5.8 Hz, 1H), 3.77 (dd, J=17.6, 5.0 Hz, 1H), 3.40-3.35 (m, 1H), 3.09-2.93 (m, 2H), 2.70-2.54 (m, 3H), 2.28-2.20 (m, 1H), 2.02-1.94 (m, 1H), 1.87-1.77 (m, 1H), 1.60-1.51 (m, 1H), 1.05-0.96 (m, 4H), 0.70 (dd, J=6.5, 4.4 Hz, 6H). LCMS [m+H]⁺ 492.4, RT 3.46 min (Method 3).

Example 9

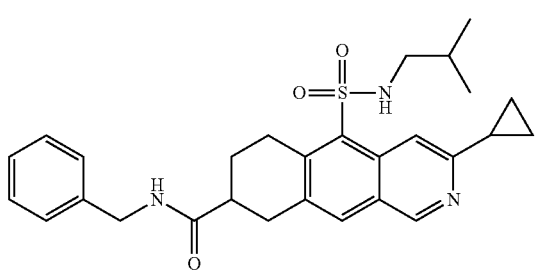
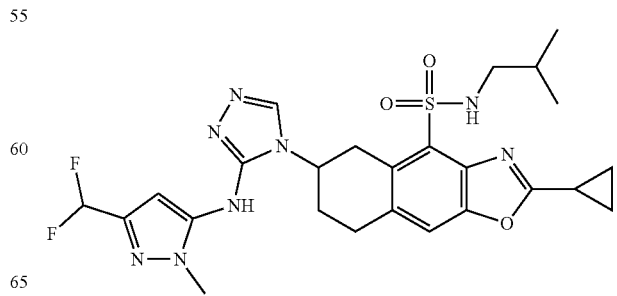

2-cyclopropyl-6-[3-[[5-(difluoromethyl)-2-methylpyrazol-3-yl]amino]-1,2,4-triazol-4-yl]-N-(2-methylpropyl)-5,6,7,8-tetrahydrobenzo[f][1,3]benzoxazole-4-sulfonamide Intermediate 48 (45 mg, 81.4 µmol) was dissolved in dichloromethane (1 mL) and triethylamine (34.0 µL, 0.244 mmol) followed by methanesulfonyl chloride (6.9 µL, 89.6 µmol) were added. The reaction mixture was stirred at room temperature for 45 minutes. Further methanesulfonyl chloride (3.2 µL, 40.7 µmol) was added and the solution stirred for 15 minutes and then diluted with dichloromethane (10 mL). Saturated aq. NH$_4$Cl (10 mL) was added and the bi-phasic solution passed through a hydrophobic frit and concentrated under reduced pressure. The residue was treated with a solution of formic hydrazide (20 mg, 0.326 mmol) in methanol (1 mL) and stirred at room temperature for 30 minutes. Sodium carbonate (35 mg, 0.326 mmol) was added and the mixture was heated to 40° C. with stirring for 16 hours. The mixture was concentrated under reduced pressure, dissolved in a 9:1 mixture of dichloromethane and methanol (10 mL) and washed with water (10 mL). The aqueous layer was extracted with a 9:1 mixture of dichloromethane and methanol (5 mL) and the combined organic extracts were passed through a hydrophobic frit. The solution was concentrated under reduced pressure and the resiude purified by column chromatography with a gradient of methanol in dichloromethane to give the title compound (26 mg, 57% Yield). δ$_H$ (500 MHz, d$_6$-DMSO) 12.03 (s, 1H, Rotamer 1), 8.83 (s, 1H, Rotamer 2), 8.43-8.14 (m, 1H), 7.72 (s, 1H), 7.45 (t, J=6.0 Hz, 1H), 6.76 (t, J=55.1 Hz, 1H), 6.23 (s, 1H), 4.50 (s, 1H), 3.91 (dd, J=17.0, 3.6 Hz, 1H), 3.66-3.55 (m, 3H), 3.24 (dd, J=16.8, 10.7 Hz, 1H), 3.18-3.12 (m, 2H), 2.76-2.65 (m, 2H), 2.33-2.13 (m, 3H), 1.78-1.67 (m, 1H), 1.29-1.20 (m, 4H), 0.85 (d, J=6.7 Hz, 3H), 0.84 (d, J=6.7 Hz, 3H). LCMS [M+H]$^+$ 561.1, RT 3.21 min (Method 1).

Example 10

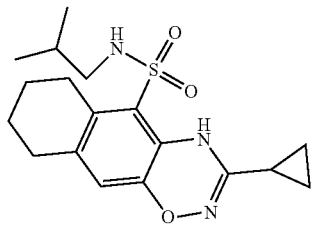 [SMILES: CC(C)CNS(=O)(=O)c1c2c(cc3c1NC(C1CC1)=NO3)CCCC2]

3-cyclopropyl-N-isobutyl-6,7,8,9-tetrahydro-4H-benzo[g][1,2,4]benzoxadiazine-5-sulfonamide Intermediate 40 (15 mg, 37.2 µmol) was dissolved in THF (1.0 mL) and Pd(PPh$_3$)$_4$ (4.3 mg, 3.72 µmol) was added. The pale yellow solution was cooled in an ice-water bath and a solution of lithiumborohydride in THF (0.04 M, 310 µL, 12.4 µmol) was added dropwise over 5 minutes. The reaction mixture was stirred in the ice bath for 1 hour before the reaction mixture was quenched with water (5 mL) and diluted with dichloromethane (5 mL). The solution was passed through a hydrophobic frit and concentrated under reduced pressure. Purification by column chromatography eluting with a gradient of ethyl acetate in heptane gave the title compound (2.2 mg, 16% Yield). δ$_H$ (500 MHz, d-chloroform) 8.75 (s, 1H), 6.63 (s, 1H), 4.56 (t, J=6.4 Hz, 1H), 2.90 (t, J=6.1 Hz, 2H), 2.73 (t, J=6.6 Hz, 2H), 2.66 (t, J=6.2 Hz, 2H), 1.80-1.68 (m, 5H), 1.54-1.51 (m, 1H), 0.97-0.87 (m, 10H). LCMS [M+H]$^+$ 364.3, RT 3.92 min (Method 1).

Example 11

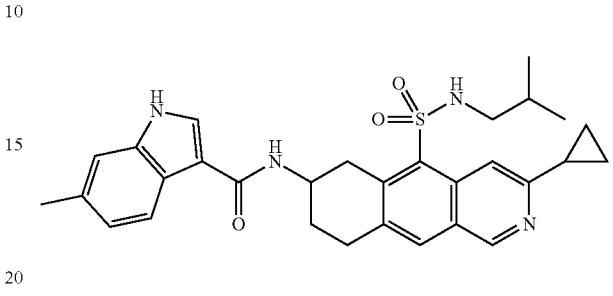

N-[3-cyclopropyl-5-(2-methylpropylsulfamoyl)-6,7,8,9-tetrahydrobenzo[g]isoquinolin-7-yl]-6-methyl-1H-indole-3-carboxamide A solution of 6-methyl-1H-indole-3-carboxylic acid (20 mg, 0.11 mmol) and DIPEA (36.2 µL, 0.21 mmol) in DCM (1 mL) was treated with HATU (104 mg, 0.27 mmol) and stirred for 5 minutes at room temperature. Intermediate 16 (40 mg, 0.1 mmol) was then added and the solution was stirred at room temperature for 2 hours. The solution was diluted with water (3 mL) and the organic layer taken. The aqueous layer was extracted with DCM (2×5 mL). The organic fractions were combined, filtered through a phase separator and the solvent removed under reduced pressure to afford a yellow powder. The powder was suspended in a 1:1 mixture of DMSO and MeOH (2 mL), filtered and the filtrate purified by column chormatography to afford the title compound as a pale-yellow gum (11 mg, 20% yield). δ$_H$ (500 MHz, d4-Methanol) 11.01 (s, 1H), 9.20 (s, 1H), 8.84 (s, 1H), 8.15 (s, 1H), 7.91 (d, J=8.2 Hz, 1H), 7.86-7.82 (m, 1H), 7.21 (s, 1H), 6.97 (d, J=8.3 Hz, 1H), 4.43-4.34 (m, 1H), 4.02 (dd, J=17.6, 4.7 Hz, 1H), 3.49 (dd, J=17.6, 9.6 Hz, 1H), 3.29-3.16 (m, 2H), 2.74-2.65 (m, 2H), 2.43 (s, 3H), 2.36-2.27 (m, 2H), 1.98-1.89 (m, 1H), 1.66-1.56 (m, 1H), 1.19-1.14 (m, 2H), 1.11-1.07 (m, 2H), 0.75 (d, J=1.5 Hz, 3H), 0.74 (d, J=1.5 Hz, 3H). LCMS [M+H]$^+$ 531.3 RT 3.51 min (Method 3).

Examples 12 & 13

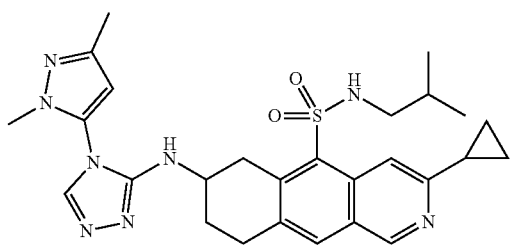

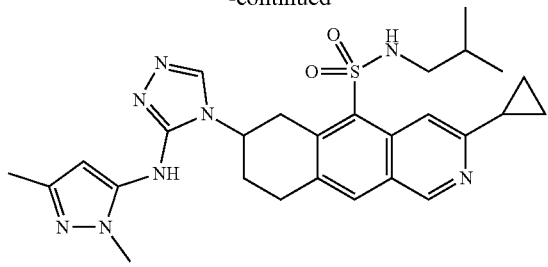

3-cyclopropyl-7-[[4-(2,5-dimethylpyrazol-3-yl)-1,2,
4-triazol-3-yl]amino]-N-(2-methylpropyl)-6,7,8,9-
tetrahydrobenzo[g]isoquinoline-5-sulfonamide (12)

3-cyclopropyl-7-[3-[(2,5-dimethylpyrazol-3-yl)
amino]-1,2,4-triazol-4-yl]-N-(2-methylpropyl)-6,7,8,
9-tetrahydrobenzo[g]isoquinoline-5-sulfonamide
(13)

To a stirred solution of intermediate 32 (60 mg, 0.097 mmol, 85% purity) in DMF (1 mL), formic hydrazide (17.4 mg, 0.29 mmol) followed by mercury dichloride (78.9 mg, 0.29 mmol) were added. The reaction mixture was stirred at room temperature for 5 minutes, then TEA (40.5 µL, 0.29 mmol) was added and the resulting suspension heated to 70° C. for 5 hours. The suspension was cooled to room temperature, diluted with DCM and kieselguhr added. The mixture was stirred for 1 minute then filtered. The solvent was removed under reduced pressure to give a pale-yellow gum, which was purified by reverse-phase HPLC (acidic conditions) to give 2 sets of fractions, which were each neutralised with aq. ammonia and the aqueous layers extracted with DCM (3×40 mL). For each set, the organic fractions were combined, dried over sodium sulphate and the solvent removed under reduced pressure. The 2 residues obtained were each dissolved in a 1:1 mixture of MeCN and water and freeze-dried to afford the title compounds:

Example 12 (4.2 mg): $\delta_H$ (500 MHz, d6-DMSO) 9.11 (s, 1H), 8.58 (s, 1H), 8.20 (s, 1H), 8.13 (t, J=5.9 Hz, 1H), 8.04 (s, 1H), 6.35 (d, J=7.5 Hz, 1H), 6.29 (s, 1H), 4.02 (dd, J=17.1, 4.4 Hz, 1H), 3.88-3.78 (m, 1H), 3.51 (s, 3H), 3.19-3.12 (m, 1H), 3.12-2.99 (m, 2H), 2.60-2.53 (m, 2H), 2.27-2.21 (m, 1H), 2.18 (s, 3H), 2.15-2.08 (m, 1H), 1.85-1.76 (m, 1H), 1.65-1.54 (m, 1H), 1.03-0.95 (m, 4H), 0.73 (d, J=6.7 Hz, 3H), 0.71 (d, J=6.7 Hz, 3H). LCMS [M+H]$^+$ 535.3 RT 2.60 min (Method 3).

Example 13 (5.5 mg): $\delta_H$ (500 MHz, d6-DMSO) 9.15 (s, 1H), 8.58-8.53 (m, 1H), 8.44-8.35 (m, 1H), 8.16-7.98 (m, 3H), 5.93-5.69 (m, 1H), 4.56-4.46 (m, 1H), 4.17-4.07 (m, 1H), 3.57-3.44 (m, 5H), 3.28-3.14 (m, 2H), 2.60-2.54 (m, 2H), 2.32-2.19 (m, 3H), 2.10-2.03 (m, 3H), 1.59-1.49 (m, 1H), 1.05-0.98 (m, 4H), 0.72-0.64 (m, 6H). LCMS [M+H]$^+$ 535.3 RT 2.31 min (Method 3).

Examples 14 & 15

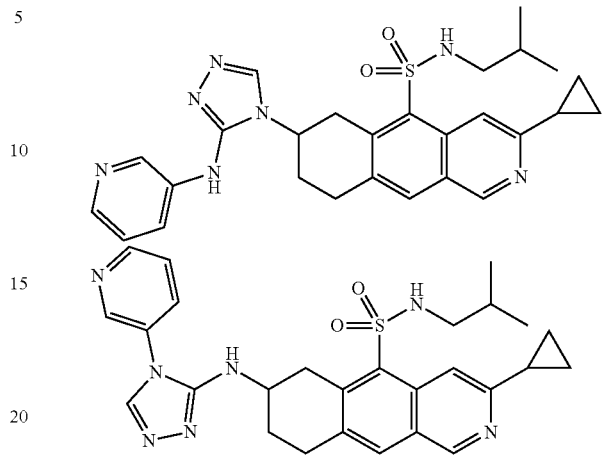

3-cyclopropyl-N-(2-methylpropyl)-7-[3-(pyridin-3-ylamino)-1,2,4-triazol-4-yl]-6,7,8,9-tetrahydrobenzo
[g]isoquinoline-5-sulfonamide (14)

3-cyclopropyl-N-(2-methylpropyl)-7-[(4-pyridin-3-yl-1,2,4-triazol-3-yl)amino]-6,7,8,9-tetrahydrobenzo
[g]isoquinoline-5-sulfonamide (15)

To a stirred solution of intermediate 31 (35 mg, 0.069 mmol) in DMF (1 mL) was added formic hydrazide (12.4 mg, 0.21 mmol), followed by mercury dichloride (55.9 mg, 0.21 mmol). The reaction mixture was stirred at room temperature for 5 minutes, then TEA (28.7 µL, 0.21 mmol) was added and the resulting suspension heated to 70° C. for 1 hour. The suspension was cooled to room temperature, diluted with DCM and kieselguhr added. The mixture was stirred for 1 minute then filtered. The solvent was removed under reduced pressure to give a pale-yellow gum. The gum was purified by reverse-phase HPLC (acidic conditions). The aqueous fractions obtained were neutralised using aqueous ammonia (to~pH 8), then extracted with DCM (3×15 mL). The organic fractions were combined, dried over sodium sulphate the solvent removed under reduced pressure to afford the title compounds:

Example 14 (2.7 mg): $\delta_H$ (500 MHz, d6-DMSO) 9.06 (s, 1H), 8.72-8.68 (m, 1H), 8.54 (s, 1H), 8.02-7.97 (m, 4H), 7.87-7.81 (m, 1H), 7.26-7.21 (m, 1H), 6.60-6.55 (m, 1H), 2.94 (t, J=7.6 Hz, 2H), 2.57 (d, J=6.8 Hz, 3H), 2.34-2.29 (m, 3H), 2.25-2.20 (m, 1H), 1.59-1.49 (m, 1H), 1.02-0.98 (m, 4H), 0.70 (d, J=6.7 Hz, 6H). LCMS [M+H]$^+$ 518.5 RT 2.83 min (Method 6).

Example 15 (3 mg): $\delta_H$ (500 MHz, d6-DMSO) 9.12 (s, 1H), 8.73 (d, J=2.5 Hz, 1H), 8.67 (dd, J=4.8, 1.3 Hz, 1H), 8.62 (s, 1H), 8.34 (s, 1H), 8.27-8.21 (m, 1H), 8.05 (s, 1H), 7.98-7.93 (m, 1H), 7.61 (dd, J=8.2, 4.8 Hz, 1H), 6.33 (d, J=7.0 Hz, 1H), 4.12 (dd, J=16.9, 4.4 Hz, 1H), 3.85-3.74 (m, 1H), 3.16-3.00 (m, 3H), 2.61-2.54 (m, 2H), 2.27-2.20 (m, 1H), 2.19-2.10 (m, 1H), 1.89-1.79 (m, 1H), 1.66-1.57 (m, 1H), 1.03-0.98 (m, 4H), 0.75 (d, J=6.7 Hz, 3H), 0.71 (d, J=6.7 Hz, 3H). LCMS [M+H]$^+$ 518.3 RT 2.38 min (Method 3).

Example 16

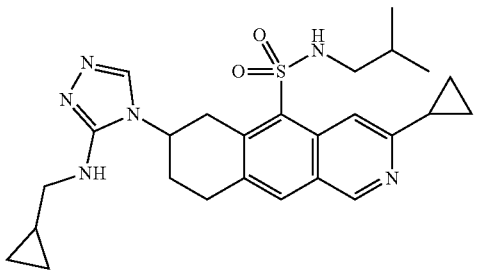 [SMILES: CC(C)CNS(=O)(=O)c1c2c(cc3cnc(C4CC4)cc13)CCC(n1cnnc1NCC1CC1)C2]

3-cyclopropyl-7-[3-(cyclopropylmethylamino)-1,2,4-triazol-4-yl]-N-(2-methylpropyl)-6,7,8,9-tetrahydrobenzo[g]isoquinoline-5-sulfonamide Intermediate 30 (55 mg, 0.06 mmol, 65% purity) was stirred in DCM (1.5 mL) and TFA (3 drops) was added. The reaction solution was stirred at room temperature for 30 minutes, then treated with TFA (4 drops). The mixture was stirred at room temperature for 2 hours, then quenched with sodium carbonate solution and the organic layer taken. The aqueous layer was extracted with DCM (2×5 mL) and the organic fractions combined and passed through a phase separator. The solution was purified by a KP—NH column, using a gradient of methanol in ethyl acetate to afford the title compound (15 mg, 53% yield) as a yellow powder. $\delta_H$ (500 MHz, d6-DMSO) 9.15 (s, 1H), 8.55 (s, 1H), 8.12 (s, 1H), 8.10 (s, 1H), 8.09-8.05 (m, 1H), 6.05 (t, J=5.7 Hz, 1H), 4.41-4.32 (m, 1H), 4.01 (dd, J=17.7, 4.7 Hz, 1H), 3.26-3.17 (m, 2H), 3.14-3.04 (m, 2H), 2.60-2.53 (m, 2H), 2.29-2.22 (m, 1H), 2.20-2.13 (m, 2H), 1.62-1.52 (m, 1H), 1.15-1.07 (m, 1H), 1.05-0.97 (m, 4H), 0.73 (d, J=3.2 Hz, 3H), 0.72 (d, J=3.2 Hz, 3H), 0.45-0.40 (m, 2H), 0.24-0.18 (m, 2H). LCMS [M+H]⁺ 495.3 RT 2.32 min (Method 3).

Examples 17 and 18

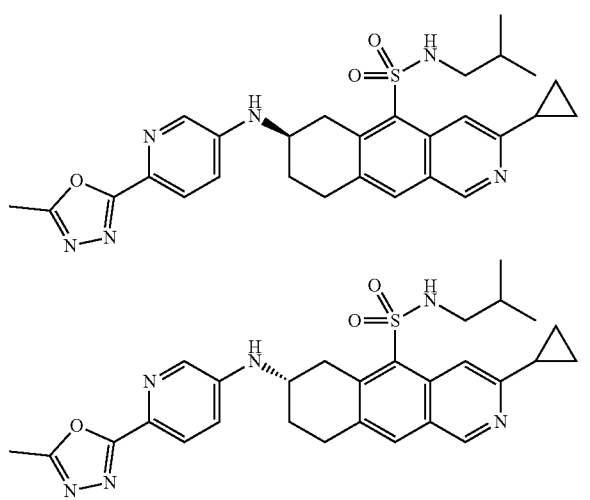

(7R)-3-cyclopropyl-7-[[6-(5-methyl-1,3,4-oxadiazol-2-yl)pyridin-3-yl]amino]-N-(2-methylpropyl)-6,7,8,9-tetrahydrobenzo[g]isoquinoline-5-sulfonamide (7S)-3-cyclopropyl-7-[[6-(5-methyl-1,3,4-oxadiazol-2-yl)pyridin-3-yl]amino]-N-(2-methylpropyl)-6,7,8,9-tetrahydrobenzo[g]isoquinoline-5-sulfonamide Intermediate 16 (138 mg, 0.24 mmol, 65% purity), intermediate 23 (80.7 mg, 0.34 mmol), tBuONa (80.8 mg, 0.84 mmol) and tBuXPhos Pd G3 (28.6 mg, 0.04 mmol) were dissolved in dioxane (6 mL) and tBuOH (3 mL) and stirred at room temperature for 2 hours. The reaction mixture was diluted with water (5 mL) and EtOAc (10 mL) and the organic layer taken. The aqueous layer was extracted with ethyl acetate (3×10 mL). The organic fractions were combined, dried over sodium sulphate and the solvent removed under reduced pressure to give an orange gum. The gum was purified by column chromatography, using a gradient of methanol in TBME to afford a pale-yellow solid. The solid was then separated by chiral chromatography to afford the title compounds:

Example 17 (24 mg): Chiral RT**=14.8 min. $\delta_H$ (500 MHz, d6-DMSO) 9.13 (s, 1H), 8.53 (s, 1H), 8.15 (d, J=2.7 Hz, 1H), 8.08 (s, 1H), 7.97 (t, J=5.9 Hz, 1H), 7.84 (d, J=8.7 Hz, 1H), 7.14 (dd, J=8.8, 2.8 Hz, 1H), 6.78 (d, J=7.5 Hz, 1H), 3.96-3.85 (m, 2H), 3.30-3.27 (m, 1H), 3.20-3.08 (m, 2H), 2.60-2.53 (m, 5H), 2.29-2.22 (m, 1H), 2.22-2.15 (m, 1H), 1.77-1.66 (m, 1H), 1.61-1.48 (m, 1H), 1.04-0.97 (m, 4H), 0.73-0.64 (m, 6H). LCMS [M+H]⁺ 533.3 RT 2.98 min (Method 3).

Example 18 (25.5 mg): Chiral RT**=24.9 min. $\delta_H$ (500 MHz, d6-DMSO) 9.13 (s, 1H), 8.53 (s, 1H), 8.15 (d, J=2.7 Hz, 1H), 8.08 (s, 1H), 7.97 (s, 1H), 7.84 (d, J=8.7 Hz, 1H), 7.14 (dd, J=8.8, 2.7 Hz, 1H), 6.78 (d, J=7.5 Hz, 1H), 3.96-3.86 (m, 2H), 3.30-3.27 (m, 1H), 3.21-3.08 (m, 2H), 2.61-2.52 (m, 5H), 2.28-2.22 (m, 1H), 2.22-2.14 (m, 1H), 1.76-1.66 (m, 1H), 1.58-1.49 (m, 1H), 1.04-0.97 (m, 4H), 0.72-0.64 (m, 6H). LCMS [M+H]⁺ 533.3 RT 2.97 min (Method 3).

** Chiral analysis was preformed using: SFC CHIRALPAK AD (250 mm×4.6) 5 μm 60/40% CO₂/(MeOH+0.5% Iso-propylamine) 2.4 mL/min 100 Bar 40° C. 5 μL at 1 mg/mL MeOH, 35 min run.

Example 19

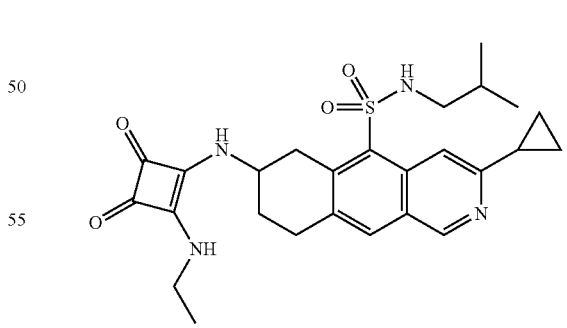

3-cyclopropyl-7-[[2-(ethylamino)-3,4-dioxocyclobuten-1-yl]amino]-N-(2-methylpropyl)-6,7,8,9-tetrahydrobenzo[g]isoquinoline-5-sulfonamide Intermediate 16 (30 mg, 0.08 mmol) was dissolved in ethanol (1 mL) and DIPEA (21.2 μL, 0.12 mmol) was added, followed by 3,4-diethoxycyclobut-3-ene-1,2-dione (17.8 µL, 0.12 mmol). The solution was stirred at room temperature for 30 minutes. 2 M ethanamine in THF (64.3 µL) was added and the solution was stirred at room temperature for 20 hours. The mixture was concentrated under reduced pressure, dissolved in a mixture of 1:1 DMSO and MeOH (1 mL) and the solution purified by reverse-phase HPLC (acidic conditions) to afford the title compound (15.7 mg, 39% yield) as a white powder. $\delta_H$ (500 MHz, d6-DMSO) 9.13 (s, 1H), 8.54 (s, 1H), 8.08 (s, 1H), 8.01 (br s, 1H), 7.58 (br s, 1H), 7.37 (br s, 1H), 4.38-4.24 (m, 1H), 3.88-3.79 (m, 1H), 3.57-3.48 (m, 2H), 3.19-3.04 (m, 2H), 2.62-2.54 (m, 2H), 2.28-2.22 (m, 1H), 2.21-2.12 (m, 1H), 1.86-1.76 (m, 1H), 1.61-1.51 (m, 1H), 1.15 (t, J=7.2 Hz, 3H), 1.03-0.98 (m, 4H), 0.72 (d, J=2.2 Hz, 3H), 0.70 (d, J=2.2 Hz, 3H). LCMS [M+H]$^+$ 497.3 RT 3.03 min (Method 6).

Example 20

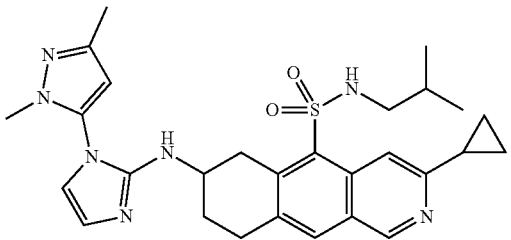 [SMILES: Cc1cc(-n2ccnc2NC2CCc3cc4cnc(C5CC5)cc4c(S(=O)(=O)NCC(C)C)c3C2)n(C)n1]

3-cyclopropyl-74(1-(2,5-dimethylpyrazol-3-yl)imidazol-2-yl]aminol-N-(2-methylpropyl)-6,7,8,9-tetrahydrobenzo[g]isoquinoline-5-sulfonamide To a stirred solution of intermediate 32 (60 mg, 0.097 mmol, 85% purity) in DMF (1 mL) was added 2,2-diethoxyethanamine (0.04 mL, 0.29 mmol), followed by mercury dichloride (78.9 mg, 0.29 mmol). The reaction mixture was stirred at room temperature for 5 minutes, then TEA (40.5 µL, 0.29 mmol) was added and the resulting suspension heated to 70° C. for 5 hours. Para-toluene sulfonic acid hydrate (110.5 mg, 0.581 mmol) was added and the mixture stirred at 70° C. for 1 hour. The suspension was cooled to room temperature, diluted with DCM and kieselguhr added. The mixture was stirred for 1 minute then filtered. The solvent was removed under reduced pressure to afford a pale-yellow gum. The gum was dissolved in DMF (1.5 mL) and stirred at 90° C. for 2 hours, then at 110° C. for 4 hours. The reaction mixture was concentrated under reduced pressure, then dissolved in methanol (1 mL). The resulting solution was purified by reverse-phase HPLC (acidic conditions) to afford a brown gum. The gum was dissolved in a 1:1 mixture of MeCN and water and freeze-dried to afford a brown powder. The solid was dissolved in DCM, washed with saturated sodium bicarbonate (2 mL) and dried over sodium sulphate. The sample was concentrated under nitrogen to afford the title compound (6.3 mg, 12% yield) as a brown gum. $\delta_H$ (500 MHz, CDCl$_3$) 9.02 (s, 1H), 8.97 (s, 1H), 8.10-8.02 (m, 1H), 7.81 (s, 1H), 6.78 (d, J=1.3 Hz, 1H), 6.60 (d, J=1.5 Hz, 1H), 6.10 (s, 1H), 4.59-4.51 (m, 1H), 3.88 (d, J=6.0 Hz, 1H), 3.66-3.58 (m, 4H), 3.15-2.99 (m, 2H), 2.75-2.62 (m, 2H), 2.50-2.43 (m, 1H), 2.34-2.21 (m, 5H), 1.91-1.81 (m, 1H), 1.72-1.65 (m, 1H), 1.16-1.08 (m, 2H), 1.07-1.00 (m, 2H), 0.94 (d, J=6.7 Hz, 3H), 0.87 (d, J=6.7 Hz, 3H). LCMS [M+H]$^+$ 534.3 RT 2.24 min (Method 3).

Examples 21 & 22

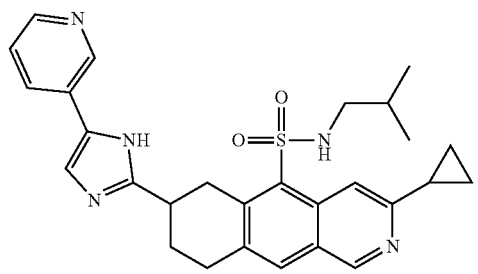

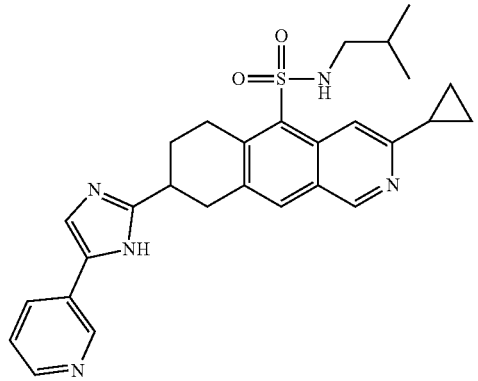

3-cyclopropyl-N-(2-methylpropyl)-7-(5-pyridin-3-yl-1H-imidazol-2-yl)-6,7,8,9-tetrahydrobenzo[g]isoquinoline-5-sulfonamide (21)

3-cyclopropyl-N-(2-methylpropyl)-8-(5-pyridin-3-yl-1H-imidazol-2-yl)-6,7,8,9-tetrahydrobenzo[g]isoquinoline-5-sulfonamide (22)

DIPEA (245 µL, 1.41 mmol) was added to a stirred solution of 2-bromo-1-(pyridin-3-yl)ethanone hydrobromide (1:1) (189 mg, 0.67 mmol) and intermediates 14 and 15 (1:1 mixture of isomers, 300 mg, 0.34 mmol, 90% purity) in MeCN (3 mL) at room temperature. The mixture was stirred at room temperature for 1.5 hours. Further DIPEA (58.4 µL, 0.34 mmol) was added and the reaction stirred at room temperature for 1 hour. 2-bromo-1-(pyridin-3-yl)ethanone hydrobromide (1:1) (47.1 mg, 0.17 mmol) was added and the mixture stirred at room temperature for 1 hour. The reaction mixture was concentrated under vacuum and the residue was taken up in EtOAc (20 mL), then washed with sat. aq. NaHCO$_3$ (10 mL). The aqueous layer was extracted with ethyl acetate (2×10 mL) and the organic fractions combined, dried over sodium sulphate and the solvent removed under reduced pressure. The residue was dissolved in dry toluene (4.5 mL) and treated with ammonium acetate (255 mg, 3.35 mmol). The suspension was stirred at 110° C. for 1 hour, then diluted with toluene (2 mL), treated with ammonium acetate (128 mg, 1.68 mmol) and stirred at 110° C. for 16 hours. The solution was then cooled to room temperature and diluted with EtOAc (20 mL). The mixture was washed with sat. aq. NaHCO$_3$ (10 mL), dried over sodium sulphate and concentrated under reduced pressure. The resulting brown gum was purified by column chromatography, using a gradient of methanol in TBME to afford a yellow solid (180 mg). The solid was purified by reverse-phase HPLC (basic conditions) to afford the title compounds Example 21 (10 mg) δ$_H$ (500 MHz, d6-DMSO) 9.12 (s, 1H), 8.95 (d, J=1.7 Hz, 1H), 8.60 (s, 1H), 8.35 (dd, J=4.7, 1.6 Hz, 1H), 8.08 (s, 1H), 8.05 (dt, J=7.9, 1.9 Hz, 1H), 7.66 (s, 1H), 7.34 (dd, J=7.8, 4.8 Hz, 1H), 4.09 (s, 1H), 3.66 (dt, J=18.0, 5.3 Hz, 1H), 3.48-3.42 (m, 1H), 3.27-3.20 (m, 1H), 2.62-2.53 (m, 2H), 2.30-2.20 (m, 2H), 2.08-1.97 (m, 1H), 1.60-1.50 (m, 1H), 1.02-0.98 (m, 4H), 0.71-0.67 (m, 6H). LCMS [m+H]$^+$ 502.4, RT 3.11 min (Method 6).

Example 22 (30 mg) δ$_H$ (500 MHz, d6-DMSO) 9.10 (s, 1H), 8.94 (d, J=1.8 Hz, 1H), 8.61 (s, 1H), 8.35 (dd, J=4.7, 1.6 Hz, 1H), 8.07-8.02 (m, 2H), 7.66 (s, 1H), 7.34 (dd, J=7.9, 4.8 Hz, 1H), 3.96 (dd, J=17.7, 4.7 Hz, 1H), 3.61-3.53 (m, 1H), 3.23-3.19 (m, 1H), 3.15-3.09 (m, 2H), 2.62-2.53 (m, 2H), 2.26-2.14 (m, 2H), 2.09-2.00 (m, 1H), 1.61-1.51 (m, 1H), 1.03-0.96 (m, 4H), 0.72-0.67 (m, 6H). LCMS [M+H]$^+$ 502.4, RT 3.24 min (Method 6).

Examples 23 & 24

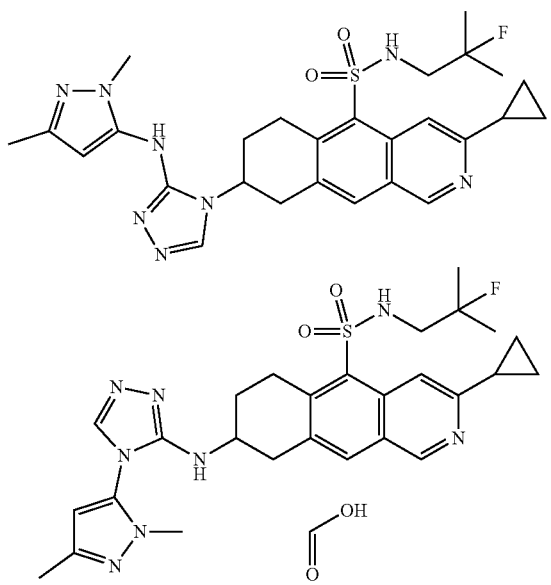

3-cyclopropyl-8-[3-[(2,5-dimethylpyrazol-3-yl) amino]-1,2,4-triazol-4-yl]-N-(2-fluoro-2-methylpropyl)-6,7,8,9-tetrahydrobenzo[g]isoquinoline-5-sulfonamide 3-cyclopropyl-8-[[4-(2,5-dimethylpyrazol-3-yl)-1,2,4-triazol-3-yl]amino]-N-(2-fluoro-2-methyl-propyl)-6,7,8,9-tetrahydrobenzo[g]isoquinoline-5-sulfonamide formic acid To a stirred solution of intermediate 28 (105 mg, 0.19 mmol) in DMF (2 mL) was added formic hydrazide (34.7 mg, 0.58 mmol), followed by mercury dichloride (157 mg, 0.58 mmol). The reaction mixture was stirred at room temperature for 5 minutes, then TEA (0.08 mL, 0.58 mmol) was added. The reaction mixture was stirred at 90° C. for 1 hour. The mixture was diluted with DCM and Kieselguhr added. The mixture was stirred for 1 minute then filtered. The filtrate was then purified by column chromatography, using a gradient of methanol in TBME to afford a pale-yellow powder. The powder was purified using reverse-phase HPLC (acidic conditions) to afford the title compounds Example 23 (15 mg); δ$_H$ (500 MHz, d6-DMSO) 9.13 (s, 1H), 8.60 (s, 1H), 8.55-8.26 (m, 2H), 8.10 (s, 1H), 6.00-5.65 (m, 1H), 4.61-4.49 (m, 1H), 3.86-3.75 (m, 1H), 3.57-3.43 (m, 5H), 3.09-2.95 (m, 2H), 2.33-2.24 (m, 2H), 2.17-2.03 (m, 4H), 1.26-1.13 (m, 6H), 1.05-0.96 (m, 4H). LCMS [m+H]$^+$553.3, RT 2.21 min (Method 3).

Example 24 (11 mg); δ$_H$ (500 MHz, d6-DMSO) 9.09 (s, 1H), 8.58 (s, 1H), 8.36-8.23 (m, 2H), 8.18 (s, 1H), 8.01 (s, 1H), 6.27-6.22 (m, 2H), 4.01-3.92 (m, 1H), 3.67-3.58 (m, 1H), 3.47 (s, 3H), 3.05-2.93 (m, 3H), 2.29-2.23 (m, 1H), 2.16 (s, 3H), 2.15-2.09 (m, 1H), 1.84-1.74 (m, 1H), 1.16 (d, J=21.4 Hz, 6H), 1.03-0.97 (m, 4H). LCMS [M+H]$^+$ 553.3, RT 2.35 min (Method 3).

In vitro Biochemical Assay:

Protocol for preparation of IgE-Tb reagent 86 nmoles of IgE-Fc(N265Q, N371Q) (Young et al., 1995) at 172 µM in 100 mM NaHCO$_3$, pH 9.5 was added to 1 mg of LanthaScreen™ Amine Reactive Tb Chelate (ThermoFisher catalogue number PV3583) and incubated for 16 hours at 20° C. The material was then buffer exchanged into Phosphate Buffered Saline (being, 137 mM NaCl, 2.7 mM KCl, 10 mM Na$_2$HPO$_4$, 1.8 mM K$_2$HPO$_4$, pH 7.4) and the material quantified and the degree of Tb conjugation determined by measuring the absorption at 280 nm and 343 nm.

The integrity of the conjugated material was determined by analytical size exclusion chromatography on a 5200 HR 10×300 column (GE Healthcare). Typical conjugation ratios were 4:1 Tb:IgE-Fc.

Young R J., Owens, R J., MacKay G A., Chan C M W., Shi J., Hide M., Francis D M., Henry A J., Sutton B J., and Gould H J (1995) Protein Engineering 8:193-199

Protocol for preparation of sFcεR1α-Y131A-AF488 reagent 400 nmoles FcεR1α (Y131A mutant) (Cook et al., 1997) at 400 µM in 100 mM NaOAc pH 5.5 was reacted with 1 mM final concentration sodium periodate (in 100 mM NaOAc, pH 5.5) for 60 minutes at 22° C. Oxidation was quenched with the addition of 40 µl of ethanediol and incubation for 60 minutes at 22° C. The protein was buffer exchanged in to conjugation buffer (50 mM NaHCO$_3$, 150 mM NaCl, pH 9.5) and concentrated to 750 µM.

175 nmoles of protein was added to 1 mg of Alexa Fluor™ 488 hydrazide (Invitrogen) and incubated for 16 hours at 22° C. Sodium cyanoborohydride (at 100 mM in conjugation buffer) was added to a final concentration of 1 mM and incubated for 60 minutes on ice. The protein was buffer exchanged into Phosphate Buffered Saline (being, 137 mM NaCl, 2.7 mM KCl, 10 mM Na$_2$HPO$_4$, 1.8 mM K$_2$HPO$_4$, pH 7.4) and the material quantified and the degree of Alexa Fluor™ 488 conjugation determined by measuring the absorption at 280 nm and 495 nm.

The integrity of the conjugated material was determined by analytical size exclusion chromatography on a 5200 HR 10×300 column (GE Healthcare). Typical conjugation ratios were 2:1 Alexa Fluor™488: sFcεR1α

Cook J P D., Henry A J., McDonnell J M., Owens R J., Sutton B J., and Gould H J (1997) Biochemistry 36:15579-15588

The aim was to measure binding of IgE-Tb to receptor, and the inhibition thereof by compounds, using an in vitro Fluorescence Resonance Energy Transfer (FRET) Assay.

Reagents

FRET reagents used were IgE labelled with Terbium (FRET donor), and soluble IgE receptor FcεRIα with a Y131A mutation, labelled with Alexa Fluor™ 488 (FRET acceptor). Unlabelled FcεRIα was also used to generate a background control. The assay buffer consisted of 20 mM Tris pH7.2, 150 mM NaCl, and 0.002% Tween, 1% DMSO.

Assay Reaction

For most of the examples the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by IgE-Tb diluting 10-fold in assay buffer. For the assay, 5 μl of diluted compound was added to 10 μl of IgE-Tb, followed by addition of 10111 FcεRIα-Y131A-AF488. FRET reagents FACs were 5 nM IgE-Tb, 25 nM FcεRIα-Y131A-AF488. Usually the top FAC of compound in the assay was 10 μM. The final DMSO concentration was 2%. The minimum signal (MIN) was measured by adding 5 μl unlabelled FcεRIα at 1 μM (FAC=200 nM) to the FRET reagents. The maximum FRET signal (MAX) was measured in wells containing FRET reagents but no compound.

The assay was incubated for 2 hours at room temperature, protected from light and evaporation, and with gentle agitation.

FRET Measurement

Measurement of FRET for each well was carried out by exciting at 330 nm and measuring emission at 495/520 nm using an Envision plate reader (Perkin Elmer). FRET ratio was calculated as follows:

Emission at 520/Emission at 495×1000.

The FRET ratio was used for the data analysis.

Data Analysis

Z' was calculated as follows (σ=standard deviation and μ=mean):

$1-((3 \times \sigma_{MAX})+(3 \times \sigma_{MIN}))/(\mu_{MAX}-/\mu_{MIN})$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Percent inhibition was plotted against compound concentration. IC50 values for each compound were determined using four parameter logistic fit model using the XLFIT5 software package.

For examples 9 and 10, the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by diluting 10-fold in assay buffer. For the assay, 5 μl of diluted compound was added to 10 μl of IgE-Tb and incubated for 30 minutes before the addition of 10 μl sFcεRIα-Y131A-AF488. FRET reagents FACs were 5 nM IgE-Tb, 25 nM sFcεRIα-Y131A-AF488. Usually the top FAC of compound in the assay was 10 μM. The final DMSO concentration was 2%. The minimum signal (MIN) was measured by adding 5 μl unlabelled sFcεRIα at 1 μM (FAC=200 nM) to the FRET reagents. The maximum FRET signal (MAX) was measured in wells containing FRET reagents but no compound.

The assay was incubated for 18 hours at room temperature, protected from light and evaporation, and with gentle agitation.

FRET Measurement

Measurement of FRET for each well was carried out by exciting at 337 nm and measuring emission at 490/520 nm using a PHERAstar FSX plate reader (BMG Labtech). FRET ratio was calculated as follows:

Emission at 520/Emission at 490×1000.

The FRET ratio was used for the data analysis.

Data Analysis

Z' was calculated as follows (σ=standard deviation and μ=mean):

$1-((3 \times \sigma_{MAX})+(3 \times \sigma_{MIN}))/(\mu_{MAX}-/\mu_{MIN})$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Percent inhibition was plotted against compound concentration. IC50 values for each compound were determined using four parameter logistic fit model using the XLFIT5 software package. Compounds of the invention show an IC50 value ranging from 10 nM to 3131 nM.

The table below shows the range of IC50 values for each example:

| Example Number | FRET IC$_{50}$ range |
| --- | --- |
| 8, 13, 14, 16, 19, 21 | 1-50 nanomolar |
| 5, 9, 10, 18 | 50-100 nanomolar |
| 2, 3, 4, 7, 11, 12, 15, 17, 20, 22 | 100-1000 nanomolar |
| 6, 23, 24 | 0.1-2 micromolar |

The invention claimed is:

1. A compound of formula (I) or a pharmaceutically acceptable salt thereof:

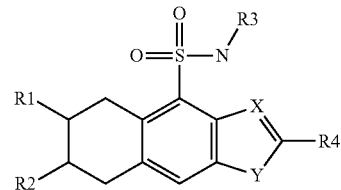

Wherein

X is C or N;

Y is —(C═N)— or —(N═N)— or O or —(O—NH)—;

R1 represents:

Hydrogen; or

Heteroaryl optionally substituted with one or more selected from the group consisting of amino; C(O)O-C1-6-alkyl;

C(O)NH-C1-6-alkyl; NH-C1-6-alkyl; NH-C1-6-alkanediyl-C3-6-cycloalkyl; heteroaryl; NH-heteroaryl optionally substituted with one or more Ra; or NHC(NCN)NH-Aryl optionally substituted with one or more Ra; or NH-heteroaryl optionally substituted with one or more groups seleted from the group consisting of C1-6-alkyl and heteroaryl optionally substituted with one or more Ra; or C(O)NH-C1-6-alkyl; or C(O)NH-C1-6-alkanediyl-aryl optionally substituted with one or more Ra; or C(O)NH-C1-6-alkanediyl-heteroaryl optionally substituted with one or more Ra; or NHC(O)heteroaryl optionally substituted with one or more Ra; or NH-C3-8-cycloalkyl substituted with one or more C1-6-alkylamino; oxo or Ra;

R2 represents:

Hydrogen; or C(O)NH-C1-6-alkyl optionally substituted with aryl optionally substituted with one or more Ra; or Heteroaryl substituted with one or more group chosen amongst heteroaryl optionally substituted with one or more Ra; heteroarylamino optionally substituted with one or more Ra; or NH-Heteroaryl subtituted with a heteroaryl optionally substituted with one or more Ra;

R3 represents:

C1-6-alkyl optionally substituted with one or more R3$^a$ groups;

C1-3-alkanediyl-C3-6-cycloalkyl optionally substituted with one or more R3$^a$ groups;

C1-3-alkanediyl-C3-6-heterocycloalkyl optionally substituted with one or more R3$^a$ groups;

C3-6-heterocycloalkyl optionally substituted with one or more R3$^a$ groups; or

C3-6-cycloalkyl optionally substituted with one or more R3$^a$ groups;

R3$^a$ represents hydrogen; halogen; C1-2-alkyl; hydroxy or C1-2-alkoxy;

R4 represents:

C3-6-cycloalkyl optionally substituted with one or more R4$^a$ group; or C1-6-alkanediyl-C3-6-cycloalkyl optionally substituted with one or more R4$^a$ group; or C1-6-alkanediyl-C3-6-heterocycloalkyl optionally substituted with one or more R4$^a$ group;

R4$^a$ represents hydroxy; halogen; or C1-2-alkyl; and

Ra represents halogen; nitrile; C1-6-alkyl; C1-6-haloalkyl; C1-6-alkoxy; C1-6-haloalkoxy; C(O)O-C1-6-alkyl or C(O)OH.

2. A compound according to claim 1, wherein X is C and Y is —(C═N)—.

3. A compound according to claim 1, wherein X is N and Y is O.

4. A compound according to claim 1, wherein X is N and Y is —(O—NH)—.

5. A compound according to claim 1, wherein R3 represents C1-6-alkyl optionally substituted with a fluorine atom.

6. A compound according to claim 1, wherein R4 represents cyclopropyl.

7. A compound according to claim 1, wherein
when R1 is not hydrogen, R2 is hydrogen;
when R2 is not hydrogen, R1 is hydrogen.

8. A compound according to claim 1 which is selected from the group consisting of:

ethyl 5-amino-1-[3-cyclopropyl-5-(2-methylpropylsulfamoyl)-6,7,8,9-tetrahydrobenzo [g] isoquinolin-7-yl-limidazole-4-carboxylate;

3-cyclopropyl-7-[3-[(2,5-dimethylpyrazol-3-yl) amino]-1,2,4-triazol-4-yl]-N-(2-fluoro-2-methylpropyl)-6,7,8, 9-tetrahydrobenzo [g] isoquinoline-5-sulfonamide;

2-Cyano-1-[3-cyclopropyl-5-[(2-fluoro-2-methyl-propyl) sulfamoyl]-6,7,8,9-tetrahydrobenzo [g] isoquinolin-7-yl]-3-(p-tolyl) guanidine;

3-cyclopropyl-N-(2-fluoro-2-methylpropyl)-7-[[6-(5-methyl-1,3,4-oxadiazol-2-yl) pyridin-3-yl] amino]-6,7, 8,9-tetrahydrobenzo [g] isoquinoline-5-sulfonamide;

3-cyclopropyl-N-(2,2-dimethylpropyl)-5-(2-methylpropylsulfamoyl)-6,7,8,9-tetrahydrobenzo [g] isoquinoline-7-carboxamide;

3-cyclopropyl-N-(2,2-dimethylpropyl)-5-(2-methylpropylsulfamoyl)-6,7,8,9-tetrahydrobenzo [g] isoquinoline-8-carboxamide;

N-benzyl-3-cyclopropyl-5-(2-methylpropylsulfamoyl)-6, 7,8,9-tetrahydrobenzo [g] isoquinoline-8-carboxamide;

N-benzyl-3-cyclopropyl-5-(2-methylpropylsulfamoyl)-6, 7,8,9-tetrahydrobenzo [g] isoquinoline-7-carboxamide;

2-cyclopropyl-6-[3-[[5-(difluoromethyl)-2-methylpyrazol-3-yl] amino]-1,2,4-triazol-4-yl]-N-(2-methylpropyl)-5,6,7,8-tetrahydrobenzo [f] [1,3] benzoxazole-4-sulfonamide;

3-cyclopropyl-N-isobutyl-6,7,8,9-tetrahydro-4H-benzo [g] [1,2,4] benzoxadiazine-5-sulfonamide;

N-[3-cyclopropyl-5-(2-methylpropylsulfamoyl)-6,7,8,9-tetrahydrobenzo [g] isoquinolin-7-yl]-6-methyl-1H-indole-3-carboxamide;

3-cyclopropyl-7-[[4-(2,5-dimethylpyrazol-3-yl)-1,2,4-triazol-3-yl] amino]-N-(2-methylpropyl)-6,7,8,9-tetrahydrobenzo [g] isoquinoline-5-sulfonamide;

3-cyclopropyl-7-[3-[(2,5-dimethylpyrazol-3-yl) amino]-1,2,4-triazol-4-yl]-N-(2-methylpropyl)-6,7,8,9-tetrahydrobenzo [g] isoquinoline-5-sulfonamide;

3-cyclopropyl-N-(2-methylpropyl)-7-[3-(pyridin-3-ylamino)-1,2,4-triazol-4-yl]-6,7,8,9-tetrahydrobenzo [g] isoquinoline-5-sulfonamide;

3-cyclopropyl-N-(2-methylpropyl)-7-[(4-pyridin-3-yl-1, 2,4-triazol-3-yl) amino]-6,7,8,9-tetrahydrobenzo [g] isoquinoline-5-sulfonamide;

3-cyclopropyl-7-[3-(cyclopropylmethylamino)-1,2,4-triazol-4-yl]-N-(2-methylpropyl)-6,7,8,9-tetrahydrobenzo [g] isoquinoline-5-sulfonamide;

(7R)-3-cyclopropyl-7-[[6-(5-methyl-1,3,4-oxadiazol-2-yl) pyridin-3-yl] amino]-N-(2-methylpropyl)-6,7,8,9-tetrahydrobenzo [g] isoquinoline-5-sulfonamide;

(7S)-3-cyclopropyl-7-[[6-(5-methyl-1,3,4-oxadiazol-2-yl) pyridin-3-yl] amino]-N-(2-methylpropyl)-6,7,8,9-tetrahydrobenzo [g] isoquinoline-5-sulfonamide;

3-cyclopropyl-7-[[2-(ethylamino)-3,4-dioxocyclobuten-1-yl] amino]-N-(2-methylpropyl)-6,7,8,9-tetrahydrobenzo [g] isoquinoline-5-sulfonamide;

3-cyclopropyl-7-[[1-(2,5-dimethylpyrazol-3-yl) imidazol-2-yl] amino]-N-(2-methylpropyl)-6,7,8,9-tetrahydrobenzo [g] isoquinoline-5-sulfonamide;

3-cyclopropyl-N-(2-methylpropyl)-7-(5-pyridin-3-yl-1H-imidazol-2-yl)-6,7,8,9-tetrahydrobenzo [g] isoquinoline-5-sulfonamide;

3-cyclopropyl-N-(2-methylpropyl)-8-(5-pyridin-3-yl-1H-imidazol-2-yl)-6,7,8,9-tetrahydrobenzo [g] isoquinoline-5-sulfonamide;

3-cyclopropyl-8-[3-[(2,5-dimethylpyrazol-3-yl) amino]-1,2,4-triazol-4-yl]-N-(2-fluoro-2-methylpropyl)-6,7,8, 9-tetrahydrobenzo [g] isoquinoline-5-sulfonamide; or 3-cyclopropyl-8-[[4-(2,5-dimethylpyrazol-3-yl)-1,2,4-triazol-3-yl] amino]-N-(2-fluoro-2-methyl-propyl)-6,7,8, 9-tetrahydrobenzo [g] isoquinoline-5-sulfonamide formic acid.

9. A pharmaceutical composition comprising a compound according to claim 1 or a pharmaceutically acceptable salt thereof.

10. A method for the treatment or prevention of disorders caused by IgE comprising administration to a patient in need thereof a compound according to claim 1 or a pharmaceutically acceptable salt thereof.

11. A method for the treatment or prevention of allergy, non-allergic mast cell responses, type 1 hypersensitivity, urticaria, or familiar sinus inflammation comprising administration to a patient in need thereof a compound according to claim 1 or a pharmaceutically acceptable salt thereof.

12. A method for the treatment or prevention of airway constriction in asthma, local inflammation in eczema, increased mucus secretion in allergic rhinitis, urticaria, or increased vascular permeability comprising administration to a patient in need thereof a compound according to claim 1 or a pharmaceutically acceptable salt thereof.

13. A method for the treatment or prevention of eosinophilic granulomatosis with polyangiitis, aspirin exacerbated respiratory disease, or cutaneous T-cell lymphoma comprising administration to a patient in need thereof a compound according to claim 1 or a pharmaceutically acceptable salt thereof.

14. A method for the treatment or prevention of allergy, non-allergic mast cell responses, type 1 hypersensitivity, urticaria, familiar sinus inflammation, eosinophilic granulomatosis with polyangiitis, aspirin exacerbated respiratory disease, or cutaneous T-cell lymphoma, which comprises the administration of a compound according to claim 1 or a pharmaceutically acceptable salt thereof in a therapeutically effective amount to a patient.

15. A compound according to claim 2, wherein
R3 represents C1-6-alkyl optionally substituted with a fluorine atom.

16. A compound according to claim 2, wherein
R4 represents cyclopropyl.

17. A compound according to claim 2, wherein
when R1 is not hydrogen, R2 is hydrogen;
when R2 is not hydrogen, R1 is hydrogen.

18. A compound according to claim 4, wherein
R3 represents C1-6-alkyl optionally substituted with a fluorine atom.

* * * * *